United States Patent
Chin et al.

(10) Patent No.: US 10,159,841 B2
(45) Date of Patent: Dec. 25, 2018

(54) SYSTEM AND METHOD FOR RATE MODULATED CARDIAC THERAPY UTILIZING A TEMPERATURE SENOR

(71) Applicant: Pacesetter, Inc., Santa Clara, CA (US)

(72) Inventors: Donald Chin, Palo Alto, CA (US); Matthew G. Fishler, Santa Cruz, CA (US); Peter M. Jacobson, Livermore, CA (US)

(73) Assignee: Pacesetter, Inc., Santa Clara, CA (US)

( * ) Notice: Subject to any disclaimer, the term of this patent is extended or adjusted under 35 U.S.C. 154(b) by 9 days.

(21) Appl. No.: 15/802,107

(22) Filed: Nov. 2, 2017

(65) Prior Publication Data

US 2018/0126161 A1     May 10, 2018

Related U.S. Application Data

(62) Division of application No. 14/712,499, filed on May 14, 2015, now Pat. No. 9,833,624.

(60) Provisional application No. 61/993,606, filed on May 15, 2014.

(51) Int. Cl.
       *A61N 1/365*     (2006.01)
       *A61N 1/375*     (2006.01)

(52) U.S. Cl.
       CPC ......... *A61N 1/3655* (2013.01); *A61N 1/3756* (2013.01)

(58) Field of Classification Search
       CPC .......................... A61N 1/3655; A61N 1/3756
See application file for complete search history.

(56) References Cited

U.S. PATENT DOCUMENTS

| | | |
|---|---|---|
| 3,867,950 A | 2/1975 | Fischell |
| 4,436,092 A | 3/1984 | Cook et al. |
| 4,543,954 A | 10/1985 | Cook et al. |
| 4,719,920 A | 1/1988 | Alt et al. |
| 4,803,987 A | 2/1989 | Calfree |
| 5,005,574 A | 4/1991 | Fearnot et al. |
| 7,925,343 B1 | 4/2011 | Min et al. |
| 7,937,148 B2 | 5/2011 | Jacobson |
| 8,543,205 B2 | 9/2013 | Ostroff |
| 8,573,062 B2 | 11/2013 | Zhao |
| 9,833,624 B2 * | 12/2017 | Chin .................... A61N 1/3756 |

(Continued)

OTHER PUBLICATIONS

Notice of Allowance dated Aug. 22, 2017; Related U.S. Appl. No. 14/712,499.

(Continued)

*Primary Examiner* — Mark W Bockelman
(74) *Attorney, Agent, or Firm* — Theresa A. Raymer

(57) ABSTRACT

A cardiac rhythm management system provides an increase in pacing rate as a combination of responses to three characteristics of a relative-temperature signal: a dip, a positive slope, and a positive magnitude. The relative-temperature signal is the difference between a short-term and a long-term temperature average. A dip produces a limited and temporary rate increase having a first proportionality. A positive slope produces a rate increase with a second proportionality. A positive magnitude produces a rate increase with a third proportionality. The dip response seeds the slope response to provide a seamless and immediate rate transition after a dip. The cardiac rhythm management system limits and filters the sum of the rate increases to provide a sensor indicated rate, which is used to stimulate the heart.

20 Claims, 21 Drawing Sheets

(56) References Cited

U.S. PATENT DOCUMENTS

2012/0109236 A1    5/2012   Jacobson
2013/0261497 A1   10/2013   Pertijs

OTHER PUBLICATIONS

Amendment filed Jul. 17, 2017; Related U.S. Appl. No. 14/712,499.
Non-Final Office Action dated Jun. 30, 2017; Related U.S. Appl. No. 14/712,499.

* cited by examiner

SYSTEM AND METHOD FOR RATE MODULATED CARDIAC THERAPY UTILIZING A TEMPERATURE SENOR

PRIORITY

This application is a Divisional application of U.S. patent application Ser. No. 14/712,499, filed May 14, 2015, now U.S. Pat. No. 9,833,624, which claims the benefit of U.S. Provisional Application No. 61/993,606 filed May 15, 2014, incorporated herein by reference in its entirety to provide continuity of disclosure.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This disclosure is directed to medical devices and methods for cardiac rhythm management. More specifically, the present invention relates to systems and methods for automatically adjusting the operating parameters of a cardiac rhythm management system.

BACKGROUND

Cardiac pacing electrically stimulates the heart when the heart's natural pacemaker and/or conduction system fails to provide synchronized atrial and ventricular contractions at appropriate rates and intervals for a patient's needs. Such bradycardia pacing provides relief from symptoms and even life support for hundreds of thousands of patients. Cardiac pacing may also give electrical overdrive stimulation intended to suppress or convert tachyarrhythmias, again supplying relief from symptoms and preventing or terminating arrhythmias that could lead to sudden cardiac death.

A temperature sensor can detect changes in a patient's blood temperature, which varies with exercise. Although certain conventional pacemakers in the past used temperature-based activity sensors to enable an increase in pacing rate in response to exercise, as described in U.S. Pat. No. 5,005,574 to Fearnot and U.S. Pat. No. 4,543,954 to Cook, each of which is incorporated herein by reference in its entirety, current conventional pacemakers generally use an accelerometer-based activity sensor to provide a rate response. Temperature-based rate response leadless pacemakers are described in U.S. Pat. No. 7,937,148 to Jacobson, U.S. Pat. No. 8,543,205 to Ostroff, and U.S. Pub. No. 2013/0261497 to Pertijs, each of which is incorporated herein by reference in its entirety. Jacobson describes a leadless cardiac pacemaker containing a rate-response temperature sensor hermetically contained within the pulse generator housing. Ostroff demonstrates response times for sensing changes in blood temperature with the temperature sensor mounted in various locations within the pulse generator. Pertijs describes a leadless pacemaker using a semiconductor temperature sensor supported by the housing.

SUMMARY OF THE DISCLOSURE

A summary of several sample aspects of the disclosure follows. It should be appreciated that this summary is provided for the convenience of the reader and does not wholly define the breadth of the disclosure. For convenience, one or more aspects or embodiments of the disclosure may be referred to herein simply as "some aspects" or "certain embodiments."

In general, the disclosure is directed to a cardiac rhythm management system, and methods for use therewith, that provides an appropriate and proportional increase in pacing rate in response to exercise, based on measurements of blood temperature. The present disclosure takes into account three characteristics of the temperature signal: (1) temperature in the right heart often manifests a dip at the onset of exercise due to cooler blood flowing to the heart from peripheral circulation; (2) as exercise continues, the slope of increasing temperature provides an indication of the rate at which muscles are working, i.e., the level of exercise; (3) in prolonged exercise a steady-state temperature plateau is often reached, where heat input from the working muscles equals heat lost by the body's natural processes for regulating temperature.

Certain conventional pacemakers took into account a fourth characteristic of the temperature signal, diurnal temperature variation. This significantly complicated the apparatus and method without providing any benefit to the exercise response. Certain embodiments of the present disclosure eliminate this parameter, reducing calculation complexity and therefore reducing power consumption, which in turn improves pacemaker longevity.

Although certain conventional pacemakers took into account a temperature dip, they responded with a rate increased by a fixed amount for a fixed time, or with a rate increased in proportion to the magnitude of the dip. Neither response is optimal. The fixed response requires a predetermined threshold for identifying a dip, which in some cases fails to identify a true onset of exercise and in other cases identifies an onset of exercise when none has occurred. The proportional response is inappropriate because the magnitude of the dip is indicative of the state of the patient's peripheral circulation, not of the level of exercise. Certain embodiments of the present disclosure advantageously provide a limited proportional response to a temperature dip, which overcomes the problems of a predetermined threshold, while avoiding over-response to deep dips indicative of poor peripheral circulation.

Certain embodiments of the present disclosure provide a dip response using a high-pass filter, such that the response diminishes progressively with time after the onset of exercise. This advantageously prevents a prolonged response for non-sustained exercise in a patient whose dip in temperature is prolonged due to poor peripheral circulation.

According to certain embodiments of the present disclosure, only a positive temperature slope is used to determine a rate response. This advantageously improves the determination of rate response to exercise as the absolute value of negative slope is not indicative of the rate of heat production, i.e. the level of exercise.

Certain conventional pacemakers measured a temperature dip with respect to a first moving baseline and a temperature magnitude with respect to a local minimum (i.e. a second moving baseline). The second moving baseline was initialized to the lowest temperature during the dip and then allowed to increase, to model the temperature response to non-sustained exercise. The magnitude response was proportional to the difference between the measured temperature and this second moving baseline, where this difference was intended to represent the effect of sustained exercise. Consequently the appropriateness of the rate response depended on the quality of the model used for the second moving baseline, as a predictor of what would occur in a given patient if a short burst of activity caused a dip but was not followed by sustained exercise.

Certain embodiments of the present disclosure advantageously do not take temperature magnitude into account until it becomes positive with respect to the relative temperature, i.e. until the temperature dip due to poor peripheral circulation has dissipated. Instead, according to certain embodiments, temperature slope is used to set the response as the dip dissipates. Advantageously, this approach does not require a second moving baseline constructed from a model intended to fit all patients. It reduces the complexity of the apparatus and method, and it also reduces the number of parameters requiring adjustment to the individual patient.

Certain embodiments provide a smooth transition in rate response when the temperature begins to climb after the initial dip. According to these embodiments, the slope response is seeded with the dip response in order to prevent an inappropriate decrease in rate response in this transition region, as the dip response decreases before the slope response is established.

Certain embodiments provide a method of operating an implanted rate adaptive cardiac rhythm management system in a patient. The method comprises acquiring a blood temperature signal with a temperature sensor implanted within the heart or associated vessels, such as the SVC, IVC, CS, pulmonary arteries and the like; determining a relative-temperature signal using the blood temperature signal; determining at least two of an onset response, short term response and a long term response using the relative-temperature signal; determining a sensor indicated rate response using the at least two of an onset response, short term response and a long term response; and generating at least one cardiac stimulation pulse using the sensor indicated rate response.

In accordance with certain embodiments herein, a leadless cardiac pacemaker is provided that comprises a hermetic housing adapted and configured to be disposed in a chamber of a human heart, at least two electrodes supported by the housing, a temperature sensor contained within the housing and configured to produce a blood temperature signal; and a processor to analyze temperatures and providing a sensor indicated rate for pacing a heart, wherein the processor is located within an interior space of the housing, coupled to the two electrodes and temperature sensor. In certain embodiments, the temperature sensor may be formed integrally with an outer surface of the housing. In other examples, the temperature sensor may be implemented as a remote sensor that wirelessly communicates with the leadless pacemaker. In certain embodiments, the temperature sensor is electrically or wirelessly coupled to the circuitry contained with the housing of the leadless pacemaker that may include a processor that analyzes temperatures and provides a sensor indicated rate. In certain other embodiments, that sensor indicated rate provided by the leadless pacemaker may then be communicated to an external device, such as a second leadless pacemaker or subcutaneous defibrillator. In yet other embodiments, the leadless pacemaker may include the temperature sensor, the temperature signal generated by the temperature sensor may be communicated to an external device, such as a second leadless pacemaker or subcutaneous defibrillator, which may contain a processor that analyzes temperatures and provides a sensor indicated rate, which may then be communicated back to the first leadless pacemaker.

In accordance with embodiments herein, an intra-cardiac medical device (ICMD) that utilizes an intra-cardiac (IC) device extension to afford dual chamber functionality is provided. According to certain embodiments, a temperature sensor and/or circuitry to analyze temperatures may be provided in the housing of the ICMD and/or in the IC device extension.

In accordance with embodiments herein, a stimulation device, such as a cardiac pacemaker and/or implantable cardioverter-defibrillator (ICD), that utilizes one or more electrically-conductive leads that traverses blood vessels and heart chambers in order to connect a housing, having electronics and a power source, of the stimulation device to electrodes affixed to the heart for the purpose of electrically exciting cardiac tissue and measuring myocardial electrical activity and/or a subcutaneous ICD that does not use endocardial, transvenous, or epicardial lead wires and can deliver defibrillation using subcutaneous electrodes, is provided. According to certain embodiments, a temperature sensor may be provided on one or more of the leads of the stimulation device and circuitry to analyze temperatures may be provided in the housing of the stimulation device. According to certain embodiments, circuitry to analyze temperatures may be provided in the housing of the stimulation device and the temperature sensor may be located in one or more devices, such as a leadless pacemaker or implantable intracardiac monitor, implanted in the heart or associated vessels, such as the SVC, IVC, CS, pulmonary arteries and the like. In certain embodiments, the temperature sensor and circuitry to analyze temperatures may be located in one or more devices, such as a leadless pacemaker or implantable intracardiac monitor, implanted in the heart or associated vessels, that is in communication with the stimulation device.

In accordance with embodiments herein, a subcutaneous ICD (SICD) that uses subcutaneous electrodes to deliver defibrillation pulses, instead of endocardial, transvenous, or epicardial lead wires is provided. According to certain embodiments, circuitry to analyze temperatures may be provided in the housing of the SICD and the temperature sensor may be located on a lead or wire implanted into the heart or an associated blood vessel, such as the SVC, IVC, CS, pulmonary arteries and the like. In certain embodiments, the temperature sensor and/or circuitry to analyze temperatures may be located in one or more devices, such as a leadless pacemaker or implantable intracardiac monitor, implanted in the heart or associated vessels, that is in communication with the SICD.

The circuitry to analyze temperatures may comprise a processor configured to determine a relative-temperature signal using the blood temperature signal; determine at least two of an onset response, short term response and a long term response using the relative-temperature signal; determine a sensor indicated rate response using the at least two of an onset response, short term response and a long term response; and generate at least one cardiac stimulation pulse, through the two electrodes, using the sensor indicated rate response.

Optionally, the sensor indicated rate response may be indicative of at least one of an overall heart rate increase and target heart rate and is based on whether the patient is in an exercise onset state, an initial phase of exercise, a sustained exercise state or a non-exercise state. Optionally, the processor may be configured to determine the onset response in connection with managing a rapid initial increase in heart rate based on an initial drop in the blood temperature, when the patient is in an exercise onset state. Optionally, the processor may be configured to determine the short term response in connection with managing a target rate of increase in the heart rate relative to a rate at which the blood temperature is increasing, wherein the short term response is indicative of a rate of change in the target heart rate that is proportional to the rate at which the blood temperature increases. Optionally, the processor may be configured to determine the long-term response in connection with managing heart rate increase during a sustained exercise state, where the processor determines the long-term response by analyzing change in the blood temperature over an extended period of time. The processor is further configured to adaptively adjust the pacing rate setting in response to the sensor indicated rate response.

This summary is not intended to be a complete description of, or limit the scope of, the invention. Alternative and additional features, aspects, and objects of the invention can be obtained from a review of the specification, the figures, and the claims.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

Figure 1A:
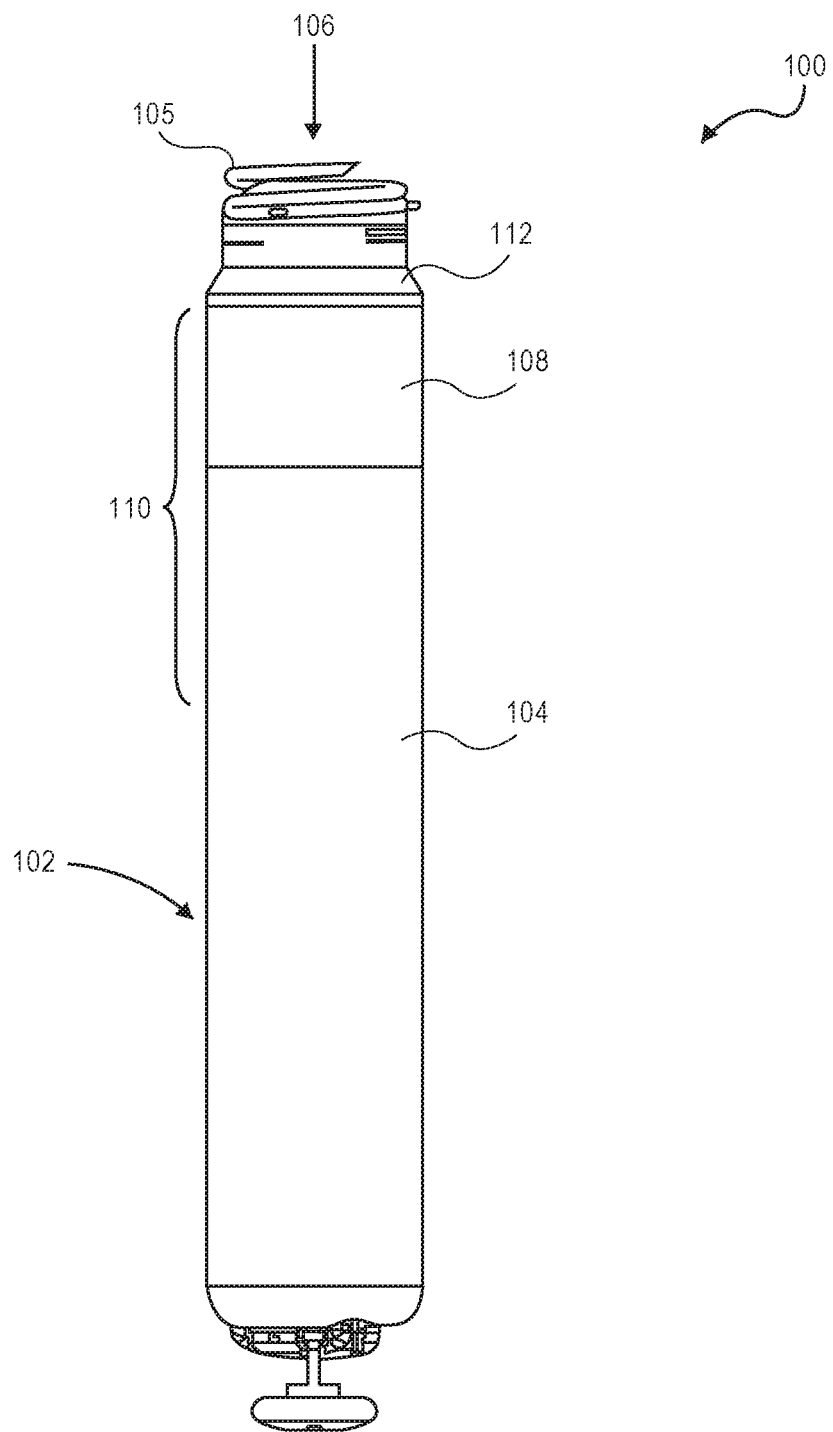
FIG. 1A is a simplified diagram of an embodiment of a leadless cardiac pacemaker.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals may be used to denote like features throughout the specification and figures.

DETAILED DESCRIPTION

The invention is described below, with reference to detailed illustrative embodiments. It will be apparent that the invention may be embodied in a wide variety of forms, some of which may appear to be quite different from those of the disclosed embodiments. Consequently, the specific structural and functional details disclosed herein are merely representative and do not limit the scope of the invention. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

This disclosure relates to cardiac rhythm management systems responsive to temperature. The cardiac rhythm management systems may include one or more implantable medical devices, including, but not limited to: a leadless cardiac pacemaker that can be implanted within a chamber of the patient's heart; an intra-cardiac implantable medical devices that utilizes an IC device extension to afford dual chamber functionality; a cardiac pacemaker and/or implantable cardioverter-defibrillator (ICD) that utilizes one or more electrically-conductive leads that traverses blood vessels and heart chambers in order to connect a canister with electronics and a power source (the can) to electrodes affixed to the heart for the purpose of electrically exciting cardiac tissue and measuring myocardial electrical activity; a subcutaneous ICD that does not use endocardial, transvenous, or epicardial lead wires to deliver defibrillation (but may employ an endocardial, transvenous, or epicardial lead wire to sense temperature) and can deliver defibrillation using subcutaneous electrodes; a temperature sensor implanted into a heart or associated blood vessels of a patient; an intracardiac monitor that includes a temperature sensor, which may be a stand-alone device or part of a lead; a master device, programmer, or an implantable cardiac monitor that does not pace the heart itself, which may contain a processor that analyzes temperatures and provides a sensor indicated rate and is in communication with another implantable medical device of the cardiac rhythm management system.

In certain embodiments, the temperature sensor and/or processor that analyzes temperatures and provides a sensor indicated rate could be employed in a micro-mechanical system ("MEMS"), such as described in U.S. Pat. No. 8,573,062 to Zhao, which is disclosed herein by reference. The MEMS can be a stand-alone device, which in some embodiments is implanted on the epicardium of the heart or into a cardiac chamber using, for example, a helix and sutures employed to affix the device directly to cardiac muscle, as described in U.S. Pat. No. 7,937,148. In embodiments not including the temperature sensor, the MEMS stand-alone device can be implanted in other locations of the body. The MEMS can be configured to communicate with a stimulation device through wireless communication, for example through conductive communication as described in U.S. Publication No. 2012/0109236 to Jacobson, by for example incorporating a communication pulse generator. In alternative embodiments, the MEMS is incorporated into an implantable lead and may communicate with the stimulation device through wired communication.

Some embodiments of a leadless cardiac pacemaker may include a hermetic housing disposed in a chamber of a human heart, a battery disposed in the housing, at least two electrodes supported by the housing, a temperature sensor enclosed or contained within the housing and a controller disposed in the housing. The controller can be adapted to sense intracardiac information using the two electrodes and to deliver stimulation energy from the battery to the electrode using temperature information from the temperature sensor. The temperature sensor may be a thermistor or a semiconductor temperature sensor incorporated into the controller.

FIG. 1A shows an external view of a leadless pacemaker or biostimulator 100. Biostimulator 100 can include a hermetic housing 102 with electrodes 104 and 106 located within, on, or near the housing 102, for delivering pacing pulses to and sensing electrical activity from the muscle of the cardiac chamber, and for bidirectional communication with at least one other device within or outside the body. In various embodiments, the electrodes 104 and 106 can be coupled on, within, or within two centimeters of the housing 102. In alternative embodiments, the electrodes 104 and 106 can be coupled on, within, or within fifteen centimeters of the housing 102. In some arrangements, the electrodes 104 and 106 can be formed integrally to an outer surface of the housing 102.

As shown, electrode 106 can be separated from but surrounded partially by a fixation mechanism 105, and the electrode 104 can be disposed on the housing 102. The fixation mechanism 105 can be a fixation helix, a plurality of hooks, barbs, or other attaching features configured to attach the pacemaker to tissue, such as heart tissue.

The housing can also include an electronics compartment 110 within the housing that contains the electronic components necessary for operation of the pacemaker, including, for example, a pulse generator, communication electronics, a battery, and a processor for operation. The hermetic housing 102 can be adapted to be implanted on or in a human heart, and can be cylindrically shaped, rectangular, spherical, or any other appropriate shapes, for example.

The housing can comprise a conductive, biocompatible, inert, and anodically safe material such as titanium, 316L stainless steel, or other similar materials. The housing can further comprise an insulator disposed on the conductive material to separate electrodes 104 and 106. The insulator can be an insulative coating on a portion of the housing between the electrodes, and can comprise materials such as silicone, polyurethane, parylene, or another biocompatible electrical insulator commonly used for implantable medical devices. In the embodiment of FIG. 1A, a single insulator 108 is disposed along the portion of the housing between electrodes 104 and 106. In some embodiments, the housing itself can comprise an insulator instead of a conductor, such as an alumina ceramic or other similar materials, and the electrodes can be disposed upon the housing.

As shown in FIG. 1A, the pacemaker can further include a header assembly 112 to isolate electrode 104 from electrode 106. The header assembly 112 can be made from PEEK, tecothane or another biocompatible plastic, and can contain a ceramic to metal feedthrough, a glass to metal feedthrough, or other appropriate feedthrough insulator as known in the art.

The electrodes 104 and 106 can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 1A, electrode 106 can be a pace/sense electrode and electrode 104 can be a return electrode. The electrode 104 can be a portion of the conductive housing 102 that does not include an insulator 108.

Several techniques and structures can be used for attaching the housing 102 to the interior or exterior wall of the heart. A helical fixation mechanism 105, can enable insertion of the device endocardially or epicardially through a guiding catheter. A torqueable catheter can be used to rotate the housing and force the fixation device into heart tissue, thus affixing the fixation device (and also the electrode 106 in FIG. 1A) into contact with stimulable tissue. Electrode 104 can serve as an indifferent electrode for sensing and pacing. The fixation mechanism may be coated partially or in full for electrical insulation, and a steroid-eluting matrix may be included on or near the device to minimize fibrotic reaction, as is known in conventional pacing electrode-leads.

Figure 1B:
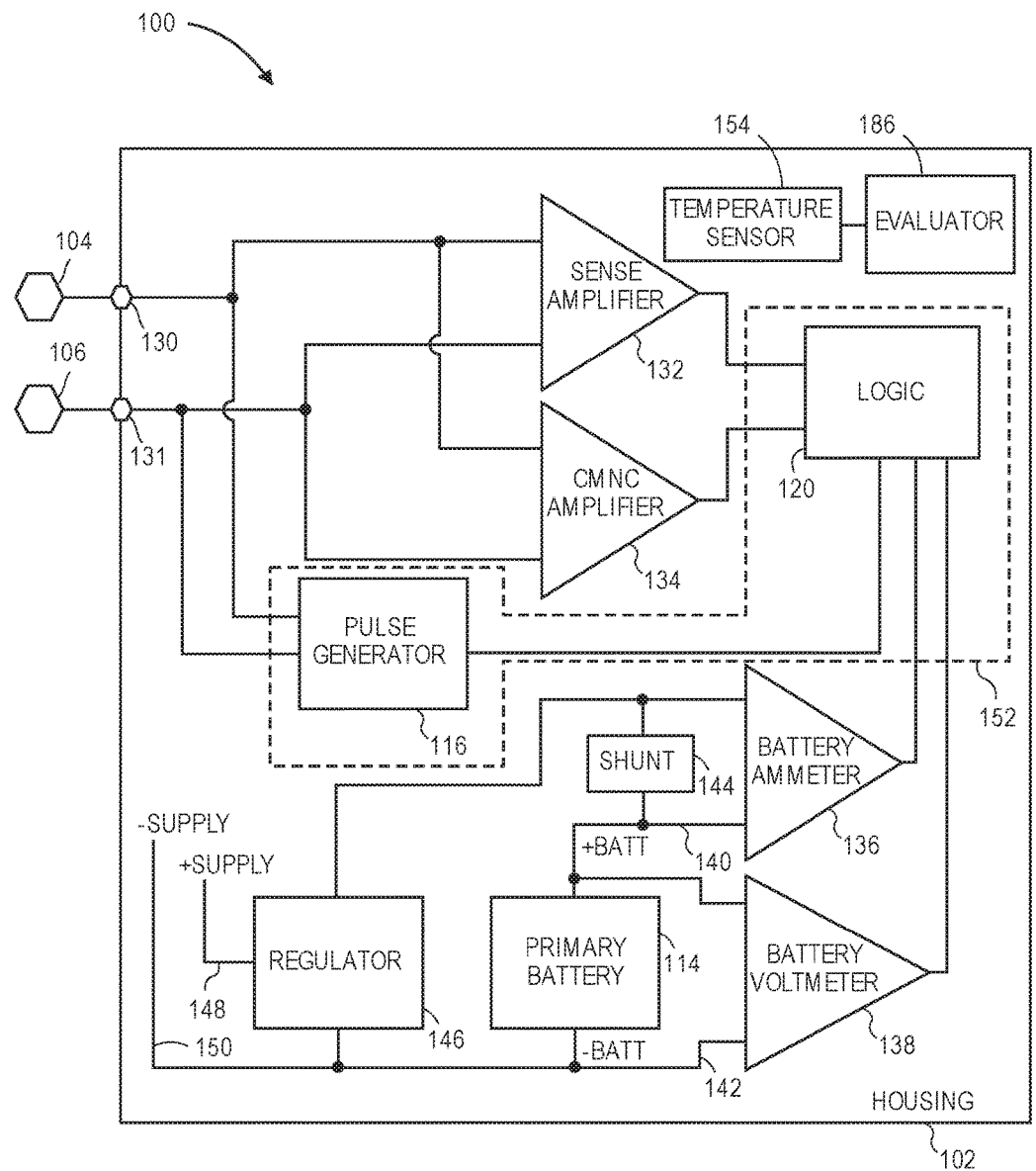
FIG. 1B is a schematic block diagram showing interconnection of operating elements of an embodiment of the illustrative rate-responsive leadless cardiac pacemaker.

Turning to FIG. 1B, a schematic block diagram depicts an embodiment of biostimulator 100. The biostimulator 100 comprises a housing 102, electrodes 104 and 106 coupled to the housing 102, a pulse delivery system 152 hermetically contained within the housing 102 and electrically coupled to the electrodes 104 and 106. The pulse delivery system 152 configured for sourcing energy internal to the housing 102, generating and delivering electrical pulses to the electrodes 104 and 106. The biostimulator 100 further comprises a temperature sensor 154 which may be enclosed within the housing 102 or may be supported by the housing 102 and adapted to sense temperature. A logic 120, for example a processor, controller, central processing unit, state machine, programmable logic array, and the like, is hermetically contained within the housing 102 and communicatively coupled to the pulse generator 116, the temperature sensor 154, and the electrodes 104 and 106. Logic 120 may control pulse generator 116 to deliver electrical pulses with the amplitudes, pulse widths, frequency, or electrode polarities specified by selected one or more therapy programs stored in a memory. Temperature sensor 154 is connected to evaluator 186. Evaluator 186 is used to provide a sensor indicated rate for pacing a heart according to certain embodiments of the disclosure. Evaluator 186 is connected to the logic 120. The sensor indicated rate output of evaluator 186 is used by logic 120 to generate control signals specifying stimulation therapy, such as pacing rate, sent to pulse generator 116.

The logic 120 and other blocks can be implemented by software, firmware, or combinations thereof. A software module may reside in RAM memory, flash memory, ROM memory, EPROM memory, EEPROM memory, registers, or any other form of storage medium known in the art. An exemplary storage medium is coupled to the processor such the processor can read information from, and write information to, the storage medium. In the alternative, the storage medium may be integral to the processor. In certain embodiments, the logic 120 comprises an application-specific integrated circuit (ASIC) and the temperature sensor 154 comprises a semiconductor temperature sensor incorporated into the ASIC. The evaluator 186 and storage medium may reside in the ASIC. In certain embodiments, logic 120 can comprise a single ultra-low power ASIC chip configured to sense, pace, and communicate. The logic 120 can control electrical pulse delivery at least partly based on the output of evaluator 186.

In some embodiments, the logic 120 can be a processor that controls electrical pulse delivery and application of the temperature sensor 154 and evaluator 186 according to one or more programmable parameters with the processor programmable by communication signals transmitted via the electrodes 104 and 106. The information communicated on the incoming communication channel can include, but is not limited to pacing rate, pulse duration, sensing threshold, and other parameters commonly programmed externally in typical pacemakers, as well as a temperature signal generated by an external temperature sensor. The information communicated on the outgoing communication channel can include, but is not limited to programmable parameter settings, event counts (pacing and sensing), battery voltage, battery current, and other information commonly displayed by external programmers used with common pacemakers, as well as a temperature signal. The outgoing communication channel can also echo information from the incoming channel, to confirm correct programming.

Hermetic feedthroughs 130, 131 conduct electrode signals through the housing 102. The housing 102 contains a primary battery 114 to provide power for pacing, sensing, and communication. The housing 102 contains circuits 132 for sensing cardiac activity from the electrodes 104 and 106; circuits 134 for receiving information from at least one other device via the electrodes 104 and 106; and a pulse generator 116 for generating pacing pulses for delivery via the electrodes 104 and 106 and also for transmitting information to at least one other device via the electrodes 104 and 106. The pacemaker 100 further contains circuits for monitoring device health, for example a battery current monitor 136 and a battery voltage monitor 138. Logic 120 controls these operations in a predetermined manner.

The primary battery 114 has positive terminal 140 and negative terminal 142. In certain embodiments, the battery is a lithium carbon monofluoride (Li/CFx) battery. Current from the positive terminal 140 of primary battery 114 flows through a shunt 144 to a regulator circuit 146 to create a positive voltage supply 148 suitable for powering the remaining circuitry of the pacemaker 100. The shunt 144 enables the battery current monitor 136 to provide the logic 120 with an indication of battery current drain and indirectly of device health.

In various embodiments, the system can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

Figure 2A:
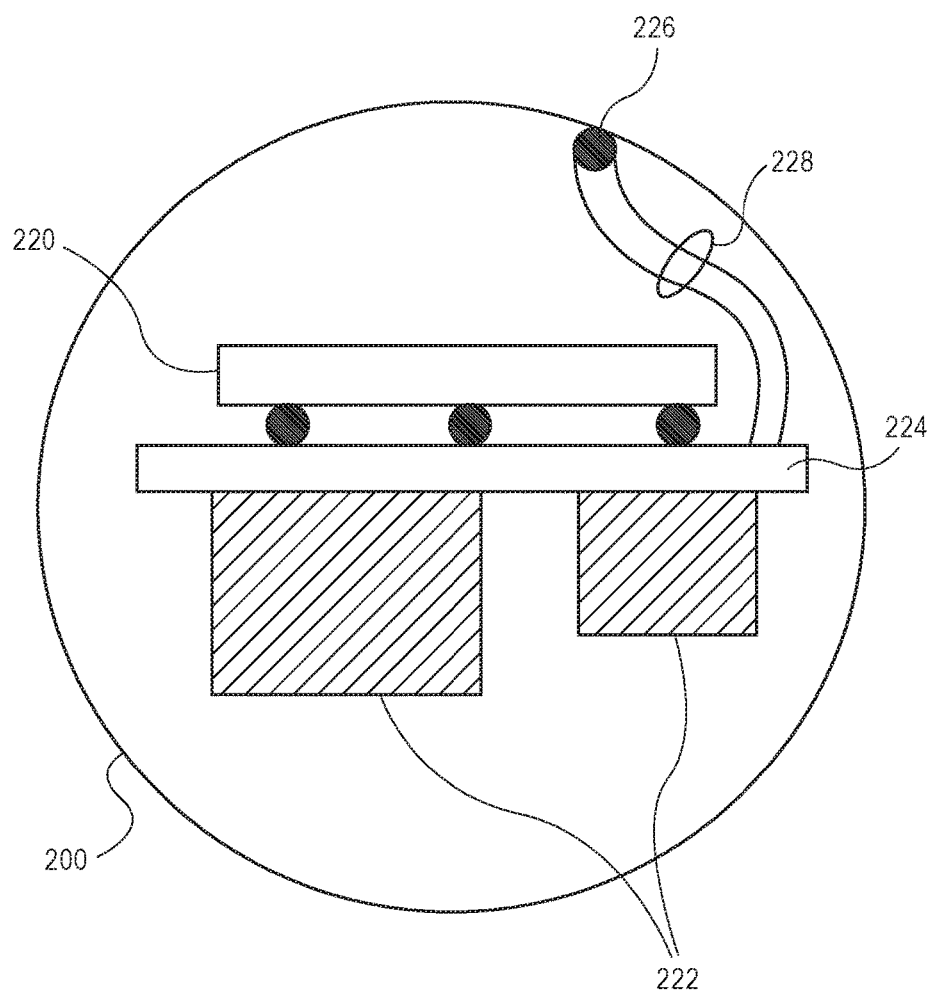
FIGS. 2A, B, and C illustrate three embodiments of a temperature sensor in a leadless cardiac pacemaker.

In the embodiment of FIG. 2A, the temperature sensor can be a thermistor 226 disposed within a housing 200. As shown in this cross-sectional view, thermistor 226 can be bonded so as to be thermally connected to an inside surface of housing 200, and the thermistors can connect to ASIC controller 220 via leads 228 and substrate 224. Thus, thermistor 226 can be configured to sense the temperature of blood surrounding the biostimulator through housing 200. Other elements within housing 200 include the ASIC substrate 224, other electronic components 222, and a battery (not shown). At least two electrodes can be supported by, and exterior to, the housing. In some embodiments, the ASIC 220 can be adapted to sense intracardiac information using the electrodes and to deliver stimulation energy from the battery to one of the electrodes using temperature information from the thermistor 226.

Figure 2B:
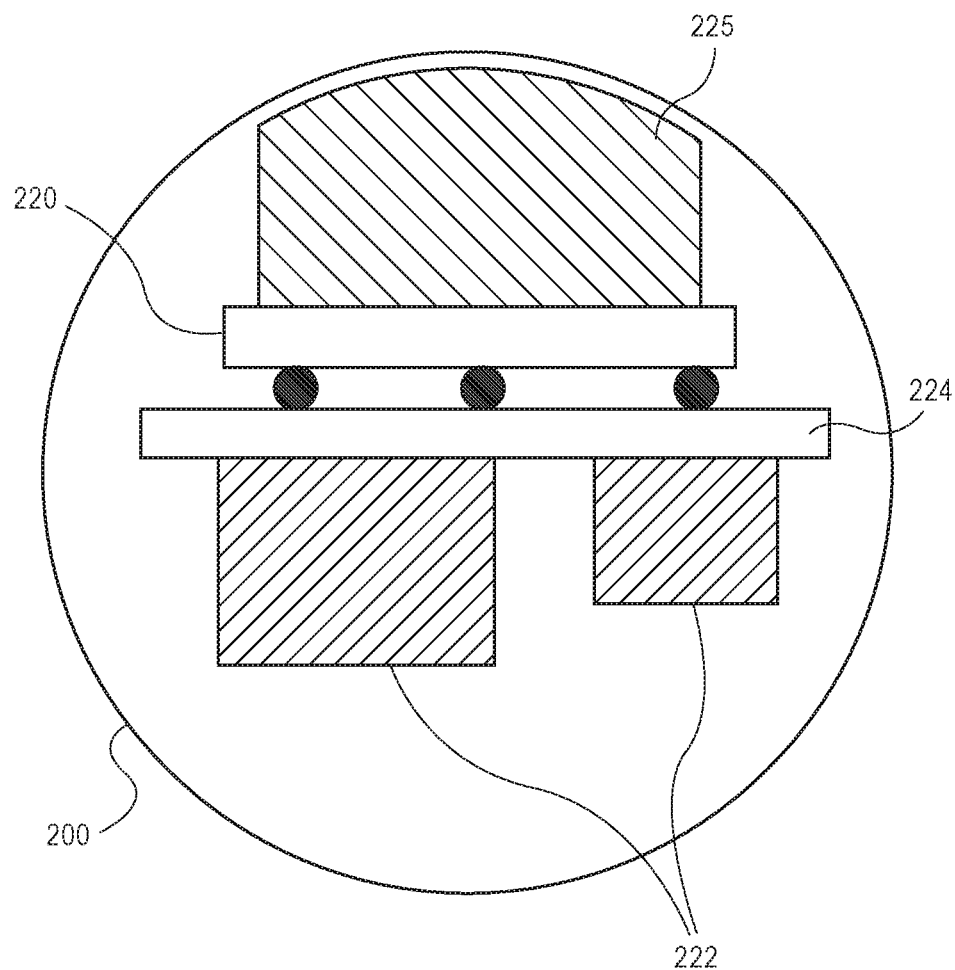

In the embodiment of FIG. 2B, the temperature sensor can be a semiconductor temperature sensor integrated into ASIC 224. A thermally conductive pad 225 can extend from the temperature sensor in ASIC 224 to an interior surface of housing 200. Thus, the temperature sensor can sense the temperature of blood surrounding the biostimulator through housing 200 with conductive pad 225. As in the embodiment of FIG. 2A, at least two electrodes can be supported by, and exterior to, the housing. The ASIC controller 220 can be adapted to sense intracardiac information using the electrodes and to deliver stimulation energy from the battery to one of the electrodes using temperature information from the integrated temperature sensor.

Figure 2C:
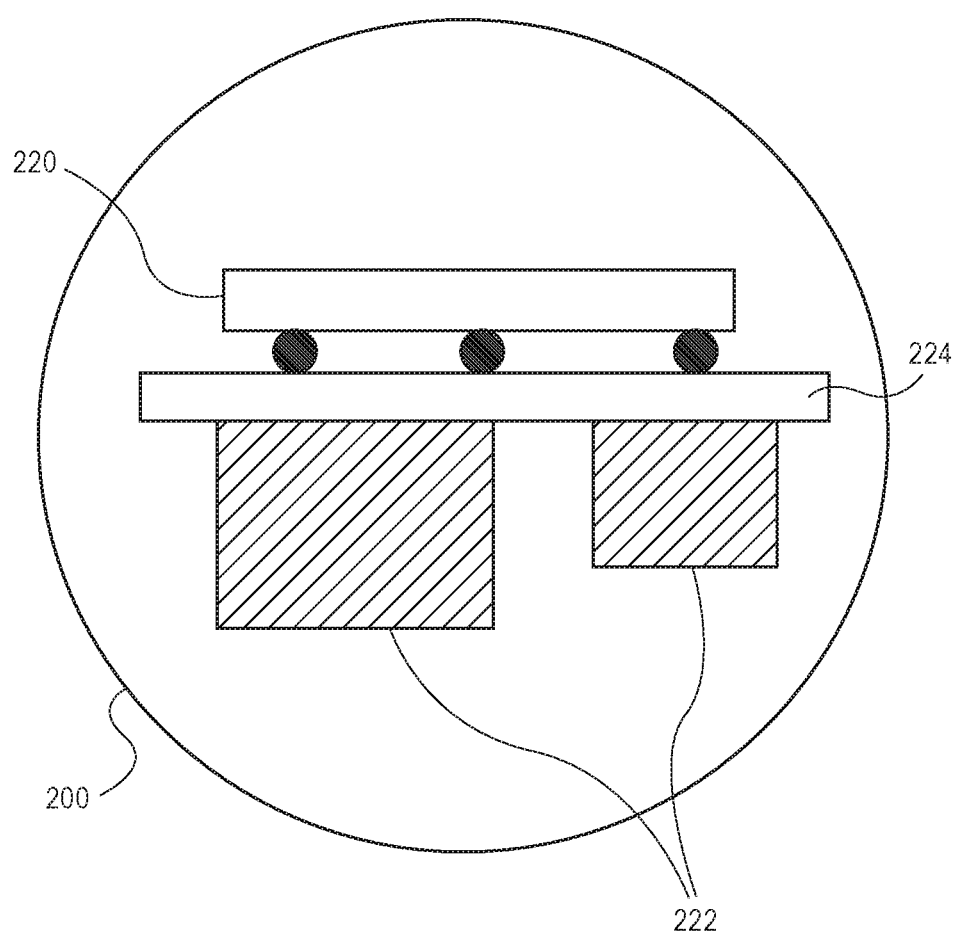

The embodiment of FIG. 2C is similar to that of FIG. 2B, but omits the thermally conductive pad. Thus, the temperature sensor integrated into ASIC 224 senses the temperature of blood surrounding the biostimulator via the thermal conductance between the ASIC 224 and the can 202. Similarly, in this embodiment, the ASIC controller 220 can be adapted to sense intracardiac information using the electrodes and to deliver stimulation energy from the battery to one of the electrodes using temperature information from the integrated temperature sensor.

Figure 3:
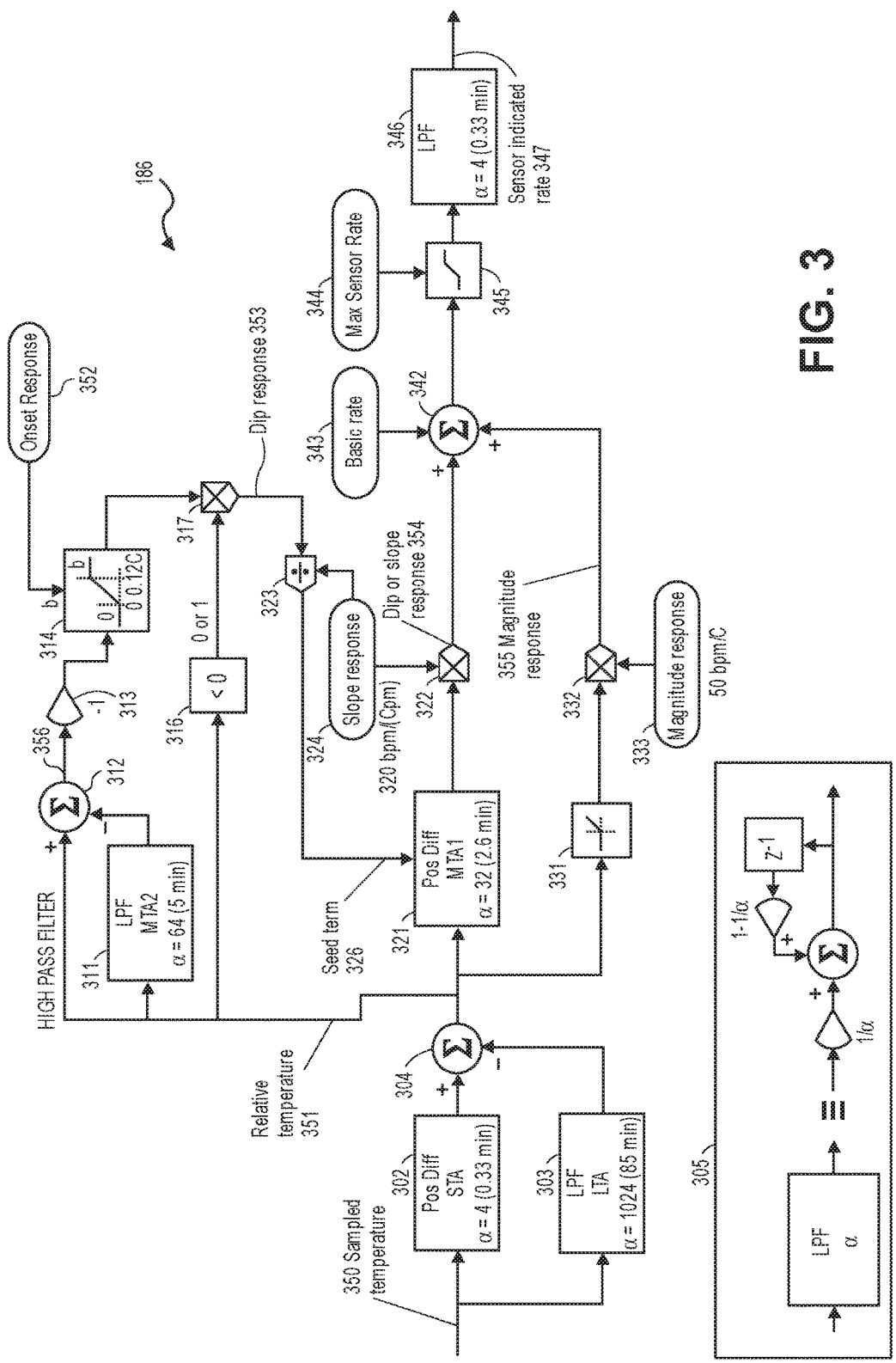
FIG. 3 is a block diagram of an embodiment of a temperature responsive controller.

Turning to FIG. 3, a block diagram illustrates a configuration of an evaluator 186 used to provide a sensor indicated rate for pacing a heart according to certain embodiments of the disclosure.

Relative Temperature

A blood-temperature signal 350 is provided from a temperature sensor to the inputs of low-pass filters 302 and 303 of the evaluator 186. Logic 120 (e.g., FIG. 1B) controls the interval in which the blood-temperature signal detected by temperature sensor is sampled by evaluator 186. In this illustrative embodiment, the blood-temperature signal is sampled at a sampling interval of five seconds.

Low pass filter (LPF) 302 provides a short term average (STA) of the blood-temperature signal 350 to the non-inverting (+) input of adder 304. In this example, LPF 302 has a time constant of 0.33 minutes. LPF 302 is intended to remove noise from the blood-temperature signal, where changes in blood temperature with a shorter interval than 0.33 minutes are attributed to noise, not exercise. LPF 302 may be a first-order low-pass filter.

LPF 303 provides a long term average (LTA) of the blood-temperature signal 350 to the inverting (−) input of adder 304. LPF 303 has a time constant of 85 minutes in certain embodiments. The output of LPF 303 is intended to follow the baseline blood temperature in the absence of exercise, where changes in blood temperature with a longer interval than 85 minutes are attributed to such factors as fever, diurnal variation, and measurement drift, not exercise. It is understood that other non-exercise factors may represent the source of longer term time constant changes.

Consequently, relative temperature signal 351, the output of adder 304, represents current blood temperature relative to the baseline value before exercise. This relative-temperature signal is intended to exclude noise and non-exercise factors such as fever, diurnal variation, and measurement drift.

Inset 305 of FIG. 3 provides details for one embodiment of an LPF of evaluator 186. In the example of inset 305, an LPF is implemented as a linear first-order recursive digital filter. The time-constant for the filter, analogous to the time constant for a resistor-capacitor (RC) electrical filter, is approximately α times the sampling interval (5 seconds). Inset 305 can implement any of the LPFs of the evaluator 186 in this example embodiment.

Relative-temperature signal 351 therefore provides a signal representing blood-temperature changes due to exercise, which is then conveyed to the inputs of three parts of the embodiment: the dip response, the slope response, and the magnitude response.

Dip Response

The dip response is implemented in this illustrative embodiment by LPF 311, adder 312, inverter 313, proportional limiter 314, comparator 316, switch 317, and dip response adjustment 352 of the evaluator 186.

LPF 311 and adder 312 are configured as a high pass filter (HPF) with a time constant of 5 minutes in the illustrated embodiment. Relative-temperature signal 351 is applied to the non-inverting (+) input of adder 312, and low-pass-filtered relative temperature is applied to the inverting (−) input of adder 312. In this manner the output of adder 312 provides the relative-temperature signal after removing components that change over intervals longer than 5 minutes; in other words, a time-decaying signal or more particularly a high-pass-filtered relative-temperature signal, at 356. Consequently a step decrease in relative temperature, i.e. a dip that occurs at the start of exercise in many patients, appears as a negative pulse at 356, which decays back to zero over a few minutes. This signal is applied to inverter 313, so that the output of inverter 313 provides a positive pulse at the onset of exercise in these patients.

The output of inverter 313 is then applied to the input of proportional limiter 314. In this example, limiter 314 provides a zero output when its input is negative, a proportional output with a slope of 16 $min^{-1}$ per 0.12° C. when its input is between 0° C. and 0.12° C., and an output of a value set by the Onset Response setting 352, which could nominally be 16 $min^{-1}$ when its input exceeds 0.12° C. (as one non-limiting example). This means that the dip response provides at most a 16 $min^{-1}$ rate increase after a dip in relative temperature, and this response decays back to zero in a few minutes. If the dip magnitude is smaller than 0.12° C., then the rate response is proportionally smaller.

In an alternative embodiment, the limiter 314 could be configured to implement a non-linear function with an output that increases when the input increases.

The Onset Response (or dip response) adjustment 352 is set to a select onset response setting (e.g., 16 $min^{-1}$ in this embodiment). An external programmer can modify this value in a manner known to those skilled in the art, or it may be pre-set at manufacturing.

Relative temperature is also applied to the input of comparator 316, which provides a logic level 1 output when relative temperature is negative (i.e., during a dip), and otherwise provides a logic level 0. Switch 317 sets the dip response to zero when its control input is at logic level 0 (i.e., at all times except during a dip). This is to block a dip response due to negative-going relative temperature at the end of exercise, where relative temperature is positive and decreasing. Consequently the output of switch 317, dip response output 353, provides a proportional, limited, and temporary rate increase in response to the dip in relative temperature that often occurs at the onset of exercise.

Slope Response

Either the dip response or slope response is provided at 354 in this illustrative embodiment, by divider 323, positive differentiator 321, multiplier 322, and slope response adjustment 324. The slope response is intended to provide a short-term response during the upswing of the temperature several minutes into exercise.

At least one element for computing the slope response is positive differentiator 321. Relative temperature 351 and seed term 326 are applied as inputs to positive differentiator 321. When relative temperature 351 is increasing, positive differentiator 321 provides an output equal to relative temperature, low-pass filtered with a time constant of 2.6 minutes in this embodiment. When relative temperature 351 is not increasing, positive differentiator 321 provides an output equal to seed term 326.

When relative temperature is increasing, this indicates that exercise is warming the blood, and the rate of increase of temperature (i.e. the slope) is an indication of the level of exercise. Multiplier 322 provides slope response at 354, a rate increase proportional to the slope of the relative temperature. The proportionality is set by slope response adjustment 324, set to 320 $min^{-1}$ per ° C. $min^{-1}$ in this embodiment. An external programmer can modify this value in a manner known to those skilled in the art, or it may be pre-set at manufacturing.

When relative temperature is not increasing, this indicates that slope response is not appropriate. In this situation, dip response 353, divided by slope response adjustment 324 in divider 323, appears at the output of positive differentiator 321 and is multiplied by slope response adjustment 324 in multiplier 322. Because divider 323 and multiplier 322 cancel each other's effects, the dip response 353 simply passes through to 354.

In the absence of a dip or a positive slope, slope response at 354 is zero. This prevents noise from appearing in the signal at 354 during this time.

During a dip, the low-pass filter in positive differentiator 321 acquires dip response 353 as its initial condition, rather than the large negative slope of the dip in relative temperature. This allows the output of positive differentiator 321 to switch seamlessly and immediately to a slope response, as soon as the relative temperature starts to increase after the minimum of the dip. For example, the following pseudo-code provides one implementation of positive differentiator 321:

```
If (in < state + α * seed):
    out = seed
    state = in − α * seed
Else:
    new_state = in/α + state* (1 − 1/α)
    out = new_state − state
    state = new_state
```

If the input is less than the internal state by a sufficient amount, the output is forced to the seed input value and the internal state tracks the input with an offset. If the input rises above the threshold, the state is updated like a conventional low-pass filter and the output is the difference of the new and old state, i.e., the slope. The initial slope is set by the offset to equal the seed. The output of positive differentiator 321 is always non-negative.

In an alternative embodiment not shown in FIG. 3, the dip response and slope response could be calculated separately and combined in a maximum value function, without seeding the slope response with the dip response.

Magnitude Response

The magnitude response is provided in this illustrative embodiment by rectifier 331, multiplier 332, and magnitude response adjustment 333. The magnitude response is intended to provide a long-term rate increase during steady-state elevated temperature, characteristic of sustained exercise.

Relative-temperature signal 351 is applied to the input of rectifier 331, which provides only the positive component of relative temperature to multiplier 332. Multiplier 332 provides magnitude response output 355, equal to the positive part of relative temperature multiplied by magnitude response adjustment 333. The magnitude response adjustment 333 is set to 50 min$^{-1}$ per ° C. in this exemplary embodiment. An external programmer can modify this value in a manner known to those skilled in the art, or it may be pre-set at manufacturing.

Sensor Indicated Rate

Adder 342 adds the basic rate adjustment 343 to the dip response 353 or slope response signal 354 and the magnitude response signal 355. Limiter 345 limits the result so that it does not exceed the max sensor rate adjustment 344. The basic rate adjustment 343 is set to 60 min$^{-1}$, and the maximum sensor rate is set to 120 min$^{-1}$ in the illustrated embodiment. These adjustments may be pre-set at manufacturing or modified via programming. Finally, LPF 346 provides the sensor indicated rate at 347, with a short-term averaging time constant of 0.33 minutes applied in this example, to prevent abrupt changes in pacing rate. The sensor indicated rate is output to logic 120, which adjusts and/or delivers therapy by sending a control signal to a pulse generator 116 for generating pacing pulses for delivery via the electrodes 104 and 106. In certain embodiments, the pacemaker may use the sensor indicated rate to adjust the pacing rate.

Although logic 120 and evaluator 186 are illustrated as separate modules of FIG. 1B, logic 120 and evaluator 186 may be incorporated into a single processing unit. Evaluator 186 and any of its components discussed in greater detail herein may be components of or modules executed by logic 120.

Figure 4A:
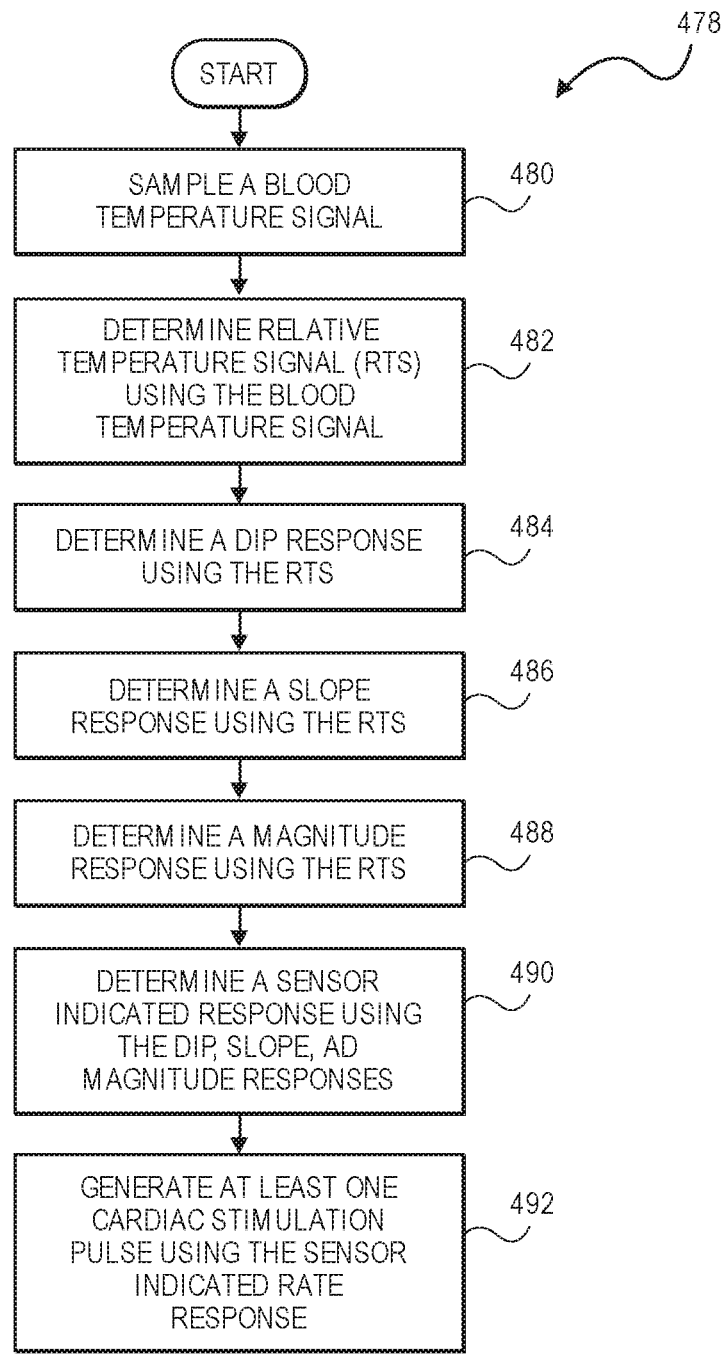
FIGS. 4A-F are schematic flow charts depicting embodiments of a method for determining a temperature sensor indicated rate in a rate responsive medical device.

FIG. 4A is a schematic flow chart depicting an embodiment of a method for setting operating parameters in a cardiac rhythm management system, such as a rate responsive cardiac pacemaker. The method 478 comprises sampling 480 a blood temperature signal using the temperature sensor, determining 482 a relative-temperature signal using the blood temperature signal, determining a dip response 484, a slope response 486, and a magnitude response 488 using the relative-temperature signal, determining 490 a sensor indicated rate response using the magnitude responses, the dip response, and the slope responses, and generating 492 at least one cardiac stimulation pulse, through electrodes of the cardiac pacemaker, using the sensor indicated rate response.

FIG. 4A and other flow charts presented herein are intended to illustrate the functional operation of the device, and should not be construed as reflective of a specific form of software, firmware, or hardware necessary to practice the methods described. It is believed that the particular form of software, firmware and/or hardware will be determined primarily by the particular system architecture employed in the device and by the particular detection and therapy delivery methodologies employed by the device. Providing software, firmware and/or hardware to accomplish the described functionality in the context of any modern medical device system, given the disclosure herein, is within the abilities of one of skill in the art.

Methods described in conjunction with flow charts presented herein may be implemented in a non-transitory computer-readable medium that includes instructions for causing a programmable processor to carry out the methods described. The instructions may be implemented as one or more software modules, which may be executed by themselves or in combination with other software.

FIGS. 4B-E illustrate detailed operations of an embodiment of a rate-responsive algorithm 400 employed to determine a sensor indicated rate.

Figure 4B:
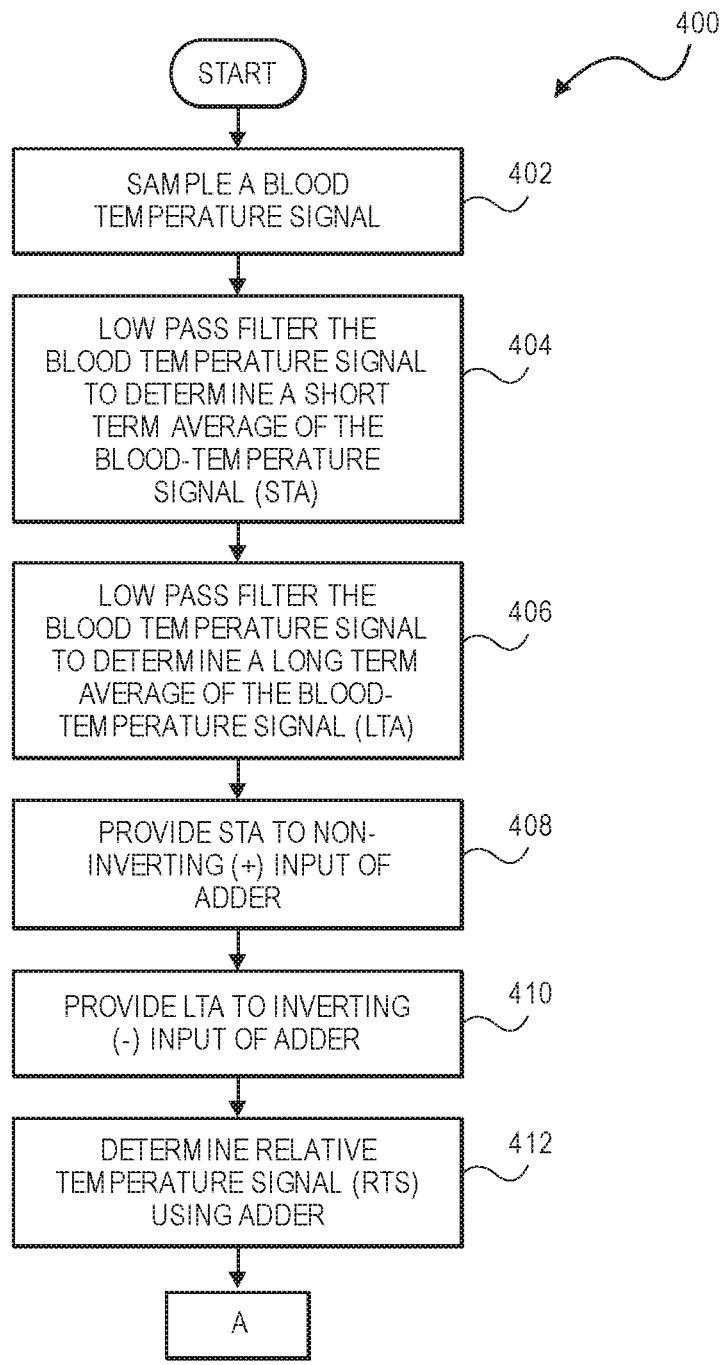

FIG. 4B illustrates the detailed operation of the rate algorithm in determining a relative temperature signal. A blood-temperature signal is sampled at block 402, at for example, a sampling interval of five seconds. The blood temperature signal is then low-pass filtered to determine a short term average (STA) of the blood-temperature signal at block 404. A first-order low-pass filter using a time constant of approximately 0.33 minutes can be used to determine the STA. The blood temperature signal is then low-pass filtered to determine a long term average (LTA) of the blood-temperature signal at block 406. A first-order low-pass filter using a time constant of approximately 85 minutes can be used to determine the LTA. The STA is provided to the non-inverting (+) input of adder 304 at block 408 and the LTA is provided to the inverting (−) input of adder 304 at block 410 to determine a relative-temperature signal (RTS) at block 412.

Figure 5:
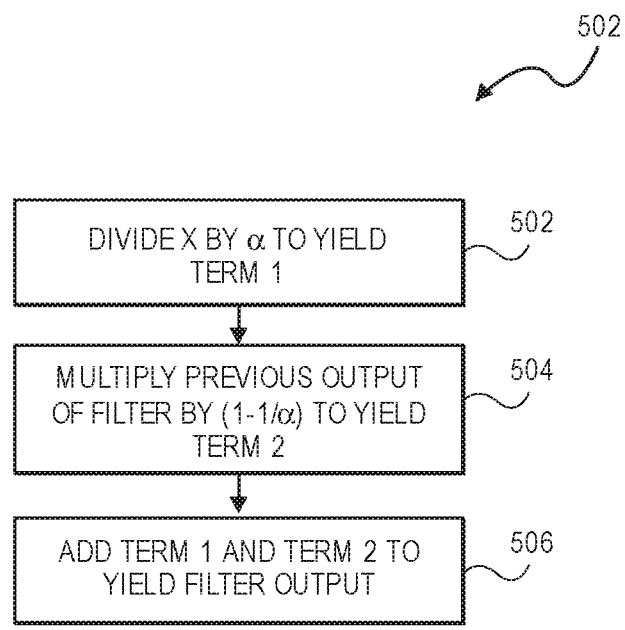
FIG. 5 is a flow chart illustrating the operation of the rate response algorithm in accordance with certain embodiments of the present disclosure.

Each low-pass filter of the evaluator, with input X and parameter α, may use a low-pass filter algorithm 500, as illustrated in FIG. 5. At 502, X is divided by a to yield term 1. At 504, the previous output of the filter, which may be obtained from memory, is multiplied by (1−1/α) to yield term 2. Terms 1 and 2 are then added to yield a filter output.

Figure 4C:
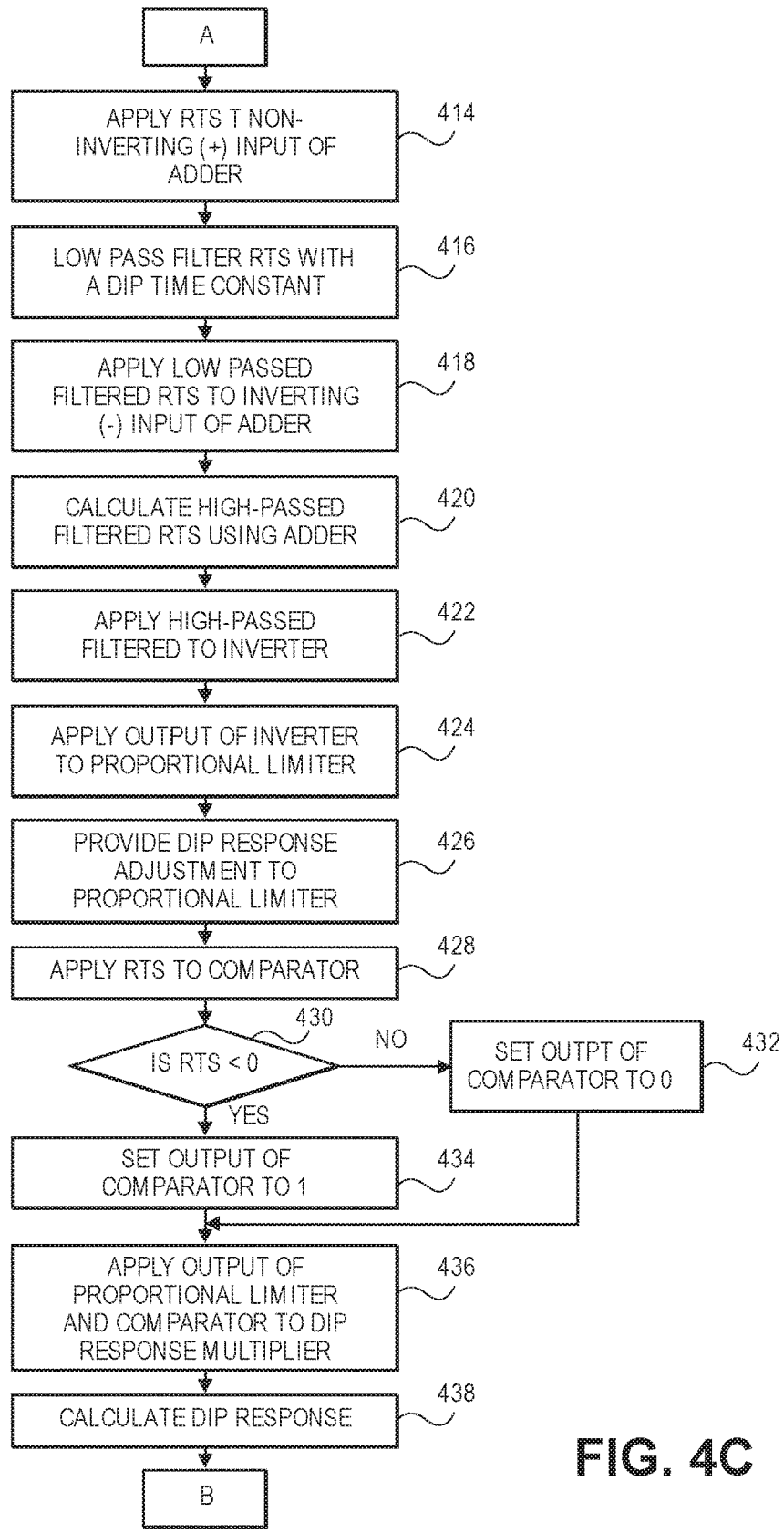

Turning to FIG. 4C, the detailed operation of the rate algorithm 400 in determining a dip response is illustrated. RTS is applied to the non-inverting (+) input of adder 312 at block 414. RTS is low passed filtered with a dip time constant of, for example five minutes at block 416. The low pass filtered RTS is applied to the inverting (−) input of adder 312 at block 418. The high-passed filtered RTS is then calculated using adder 312 at block 420. The high-passed filtered RTS is then applied to inverter 313 at block 422. The output of inverter 313 is applied to proportional limiter 314 at block 424. A dip response adjustment 352 is provided to proportional limiter 314 at block 426.

RTS is applied to the input of comparator 316 at block 428. A determination at block 430 is performed using the comparator 316 to determine whether the RTS is less than 0. At block 434, if the RTS is less than 0 (i.e., during a dip), then the output of comparator 316 is set to 1. Otherwise (i.e., at all times except during a dip), at block 432 the output of comparator 316 is set at 0.

The output of the proportional limiter 314 and comparator 316 is applied to a dip response multiplier 317 at block 436 and a dip response is calculated at block 438. In this embodiment, the dip response output provides a proportional, limited, and temporary rate increase in response to the dip in relative temperature that often occurs at the onset of exercise.

Figure 4D:
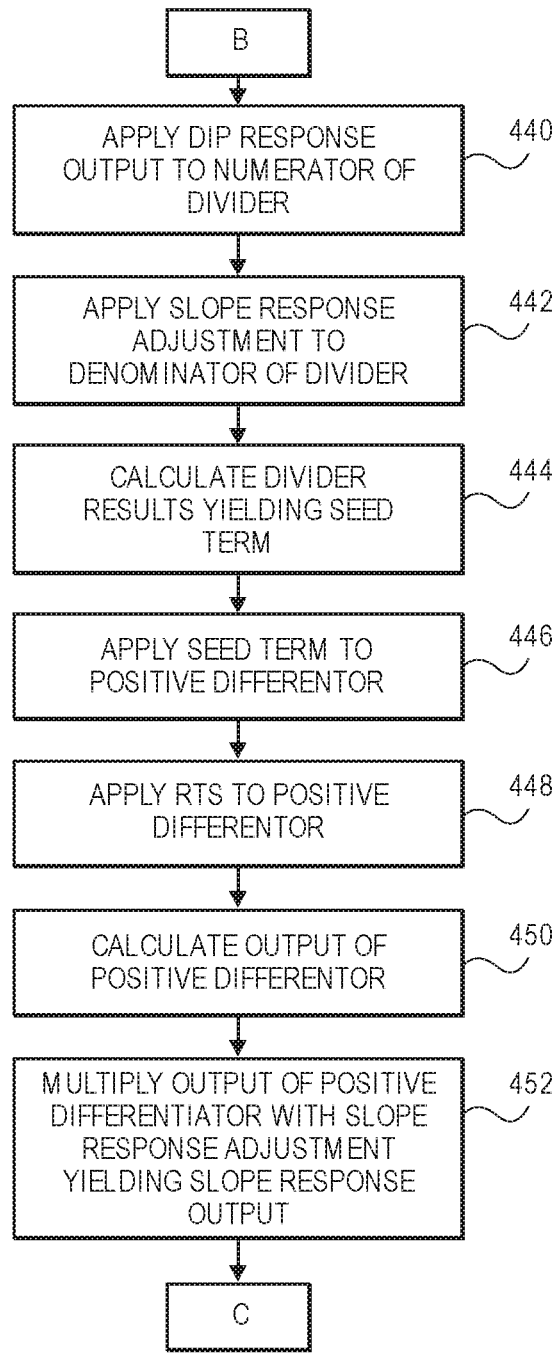

FIG. 4D illustrates the detailed operation of the rate algorithm 400 in determining a slope response. The dip response output is applied to the numerator of divider 323 at block 440. A slope response adjustment, which may, for example, be set to 320 min$^{-1}$ per ° C. min$^{-1}$, is applied to the denominator of divider 323 at block 442. The divider 323 results are calculated yielding a seed term at block 444. The seed term is applied to positive differentiator 321 at block 446. The RTS is applied to the positive differentiator 321 at block 448. The output of the positive differentiator 321 is calculated at block 450, as described in detail in FIG. 6. The output of positive differentiator 321 is multiplied with a slope response adjustment, e.g., 320 min$^{-1}$ per ° C. min$^{-1}$, yielding a slope response output at block 452, yielding a rate increase that is proportional to the slope of the relative temperature. The proportionality is set by the slope response adjustment 324, which can be set to, for example, 320 min$^{-1}$ per ° C. min$^{-1}$.

Figure 6:
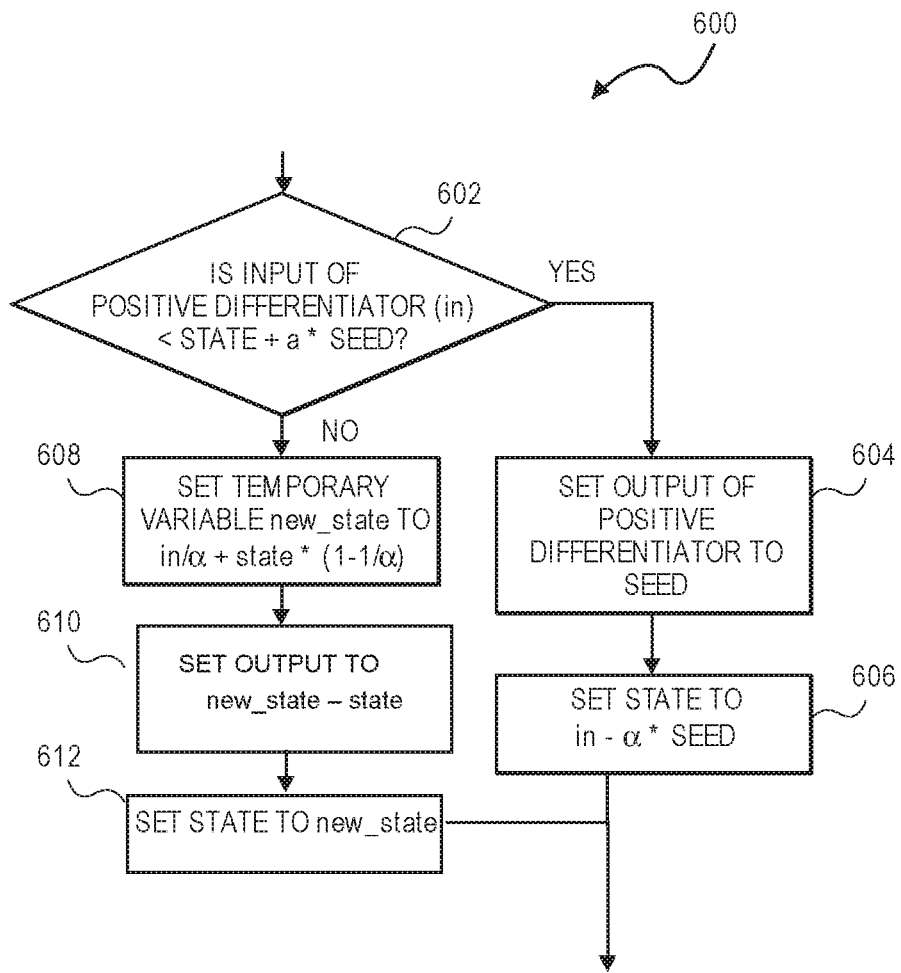
FIG. 6 is a flow chart illustrating the operation of the rate response algorithm in accordance with certain embodiments of the present disclosure.

Positive differentiator 321 of evaluator 186, with input "in" and seed parameter "seed," can use an algorithm 600, depicted in FIG. 6, to determine an output. A determination at block 602 is performed to determine whether the input of the positive differentiator (in) is less than an internal temperature variable "state" +α* seed, where the state variable may be initialized to zero. If in is not less than state +α* seed, the output of the positive differentiator 321 is set to seed at block 604 and state is set to in −α* seed at block 606. If in is less than state +α* seed, a temporary variable new_state is set to in/α+state* (1−1/α) at block 608, the output of the positive differentiator is set to new_state at block 610, and state is set to new_state at block 612.

Figure 4E:
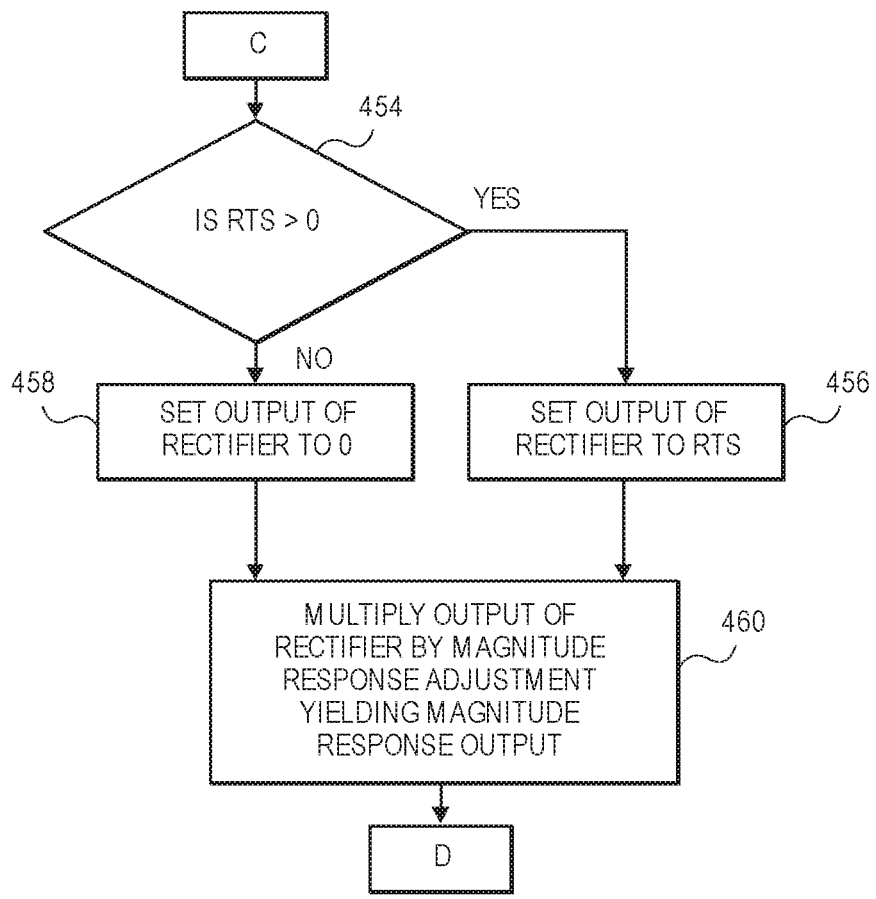

Turning to FIG. 4E, the detailed operation of the rate algorithm 400 in determining a magnitude response output is illustrated. A determination is performed at block 454 to determine whether RTS is greater than zero. If RTS is greater than zero, the output of rectifier 331 is set to RTS at block 456. If RTS is not greater than zero, the output of rectifier 331 is set to 0 at block 458. At block 460, the output of rectifier 331 is multiplied by a magnitude response adjustment 333 to yield a magnitude response output.

Figure 4F:
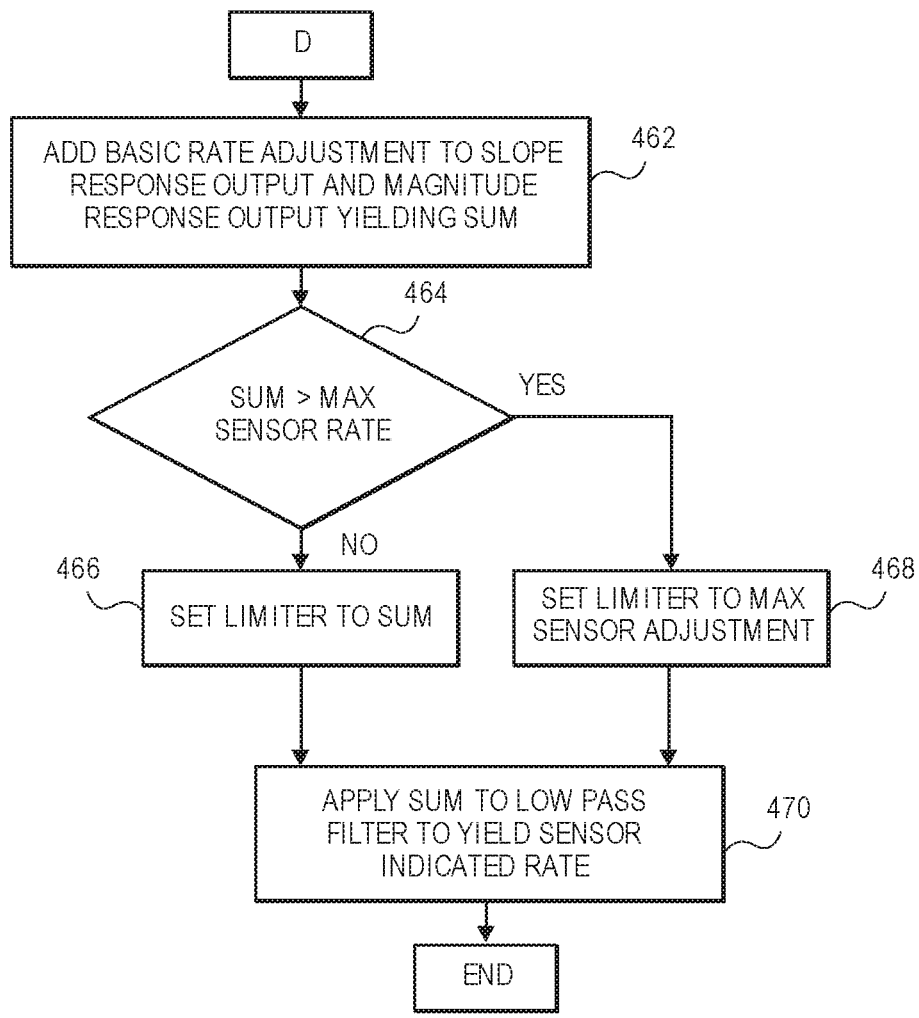

FIG. 4F illustrates the detailed operation of the rate algorithm 400 in determining a sensor indicated rate. At block 462, basic rate adjustment 343 is added to slope response output and magnitude response output yielding a sum. A determination is performed at block 464 to determine whether the sum is greater than a max sensor rate adjustment 344, which is set, for example at 120 min$^{-1}$. If the sum is not greater than the max sensor rate adjustment, the output of limiter 345 is set to the sum at block 466. If the sum is greater than the max sensor rate adjustment, the output of limiter 345 is set to the max sensor rate adjustment at block 468. At block 470, the output of limiter 345 is applied to low pass filter 346, which may for example use a short-term averaging time constant of 0.33 minutes, to yield a sensor indicated rate. Processor 120 then uses the sensor indicated rate to adjust pacing parameters of the pacemaker.

Figure 7:
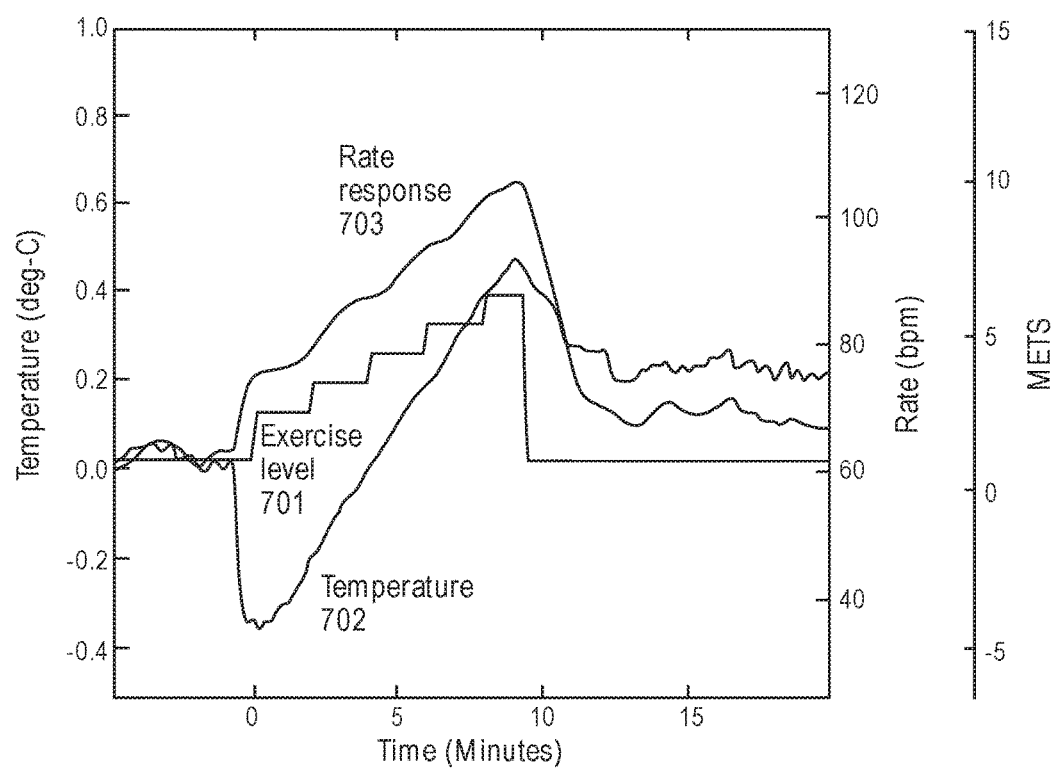
FIG. 7 is a graph useful for describing a pacemaker rate response in accordance with certain embodiments of the present disclosure.

Turning to FIG. 7, a graph of pacemaker rate response is depicted. A patient performed a graded maximal exercise test, where exercise level 701 increased each two minutes until the patient reached his or her maximum exercise level, measured in metabolic equivalents (METs). This resulted in the blood-temperature signal 702. This signal exhibited a temperature dip at onset followed by a positive slope. The pacemaker produced sensor indicated rate 703 using its dip, slope, and magnitude functions to provide rate response as described above. The pacemaker demonstrated an appropriate and proportional rate increase in response to exercise.

Effect of Seeding the Slope Response

Figure 8A:
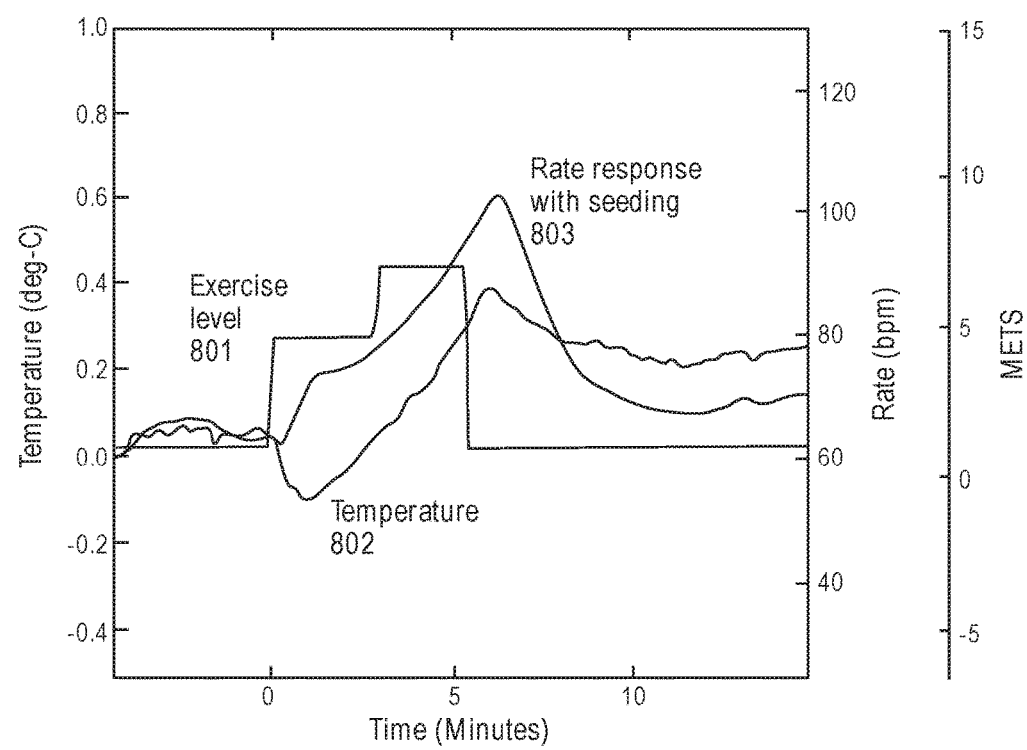
FIGS. 8A and 8B are graphs useful for describing a pacemaker rate response in accordance with certain embodiments of the present disclosure.
Figure 8B:
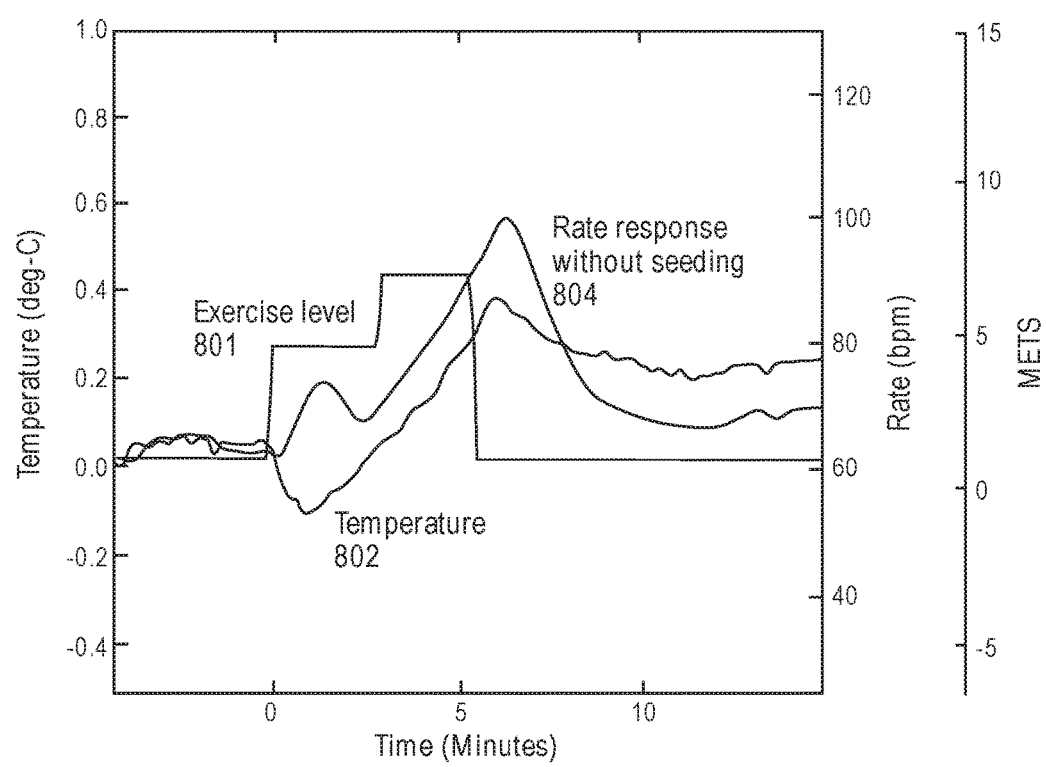

Referring to FIGS. 8A and B, graphs of pacemaker rate response with and without seeding the slope response are respectively depicted. A patient performed a graded exercise test, where exercise level 801 is measured in metabolic equivalents (METs). This resulted in the temperature signal 802. The pacemaker produced rate response 803 by seeding the slope response with the dip response as described above, and it produced rate response 804 after this feature was artificially disabled. Comparison of FIG. 8a with FIG. 8b demonstrates the value of seeding the slope response with the dip response, for providing a seamless and immediate transition between these two response regions.

Figure 9:
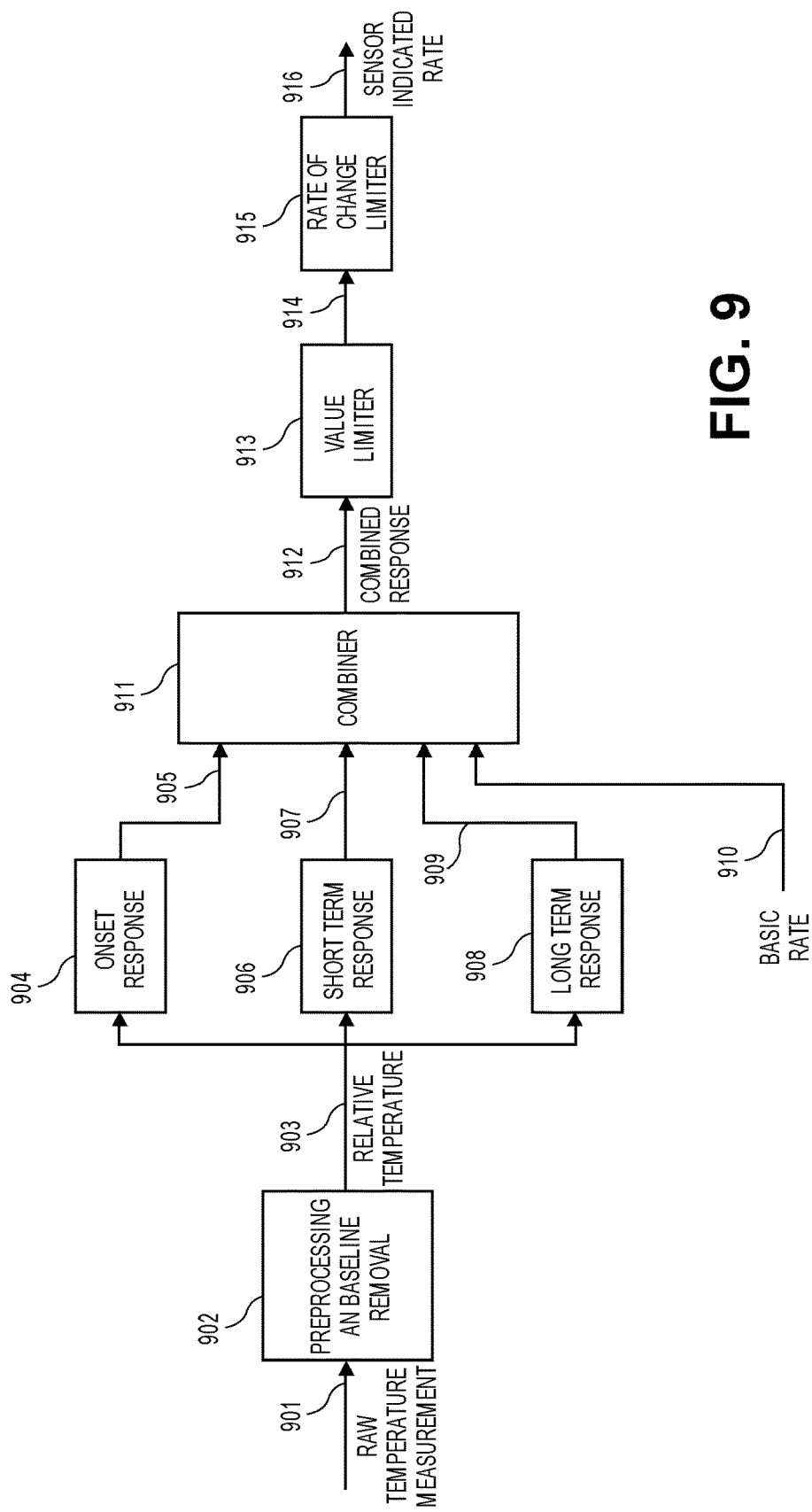
FIG. 9 illustrates a block diagram implementing a Rate Response process in accordance with various embodiments herein.

FIG. 9 illustrates a block diagram implementing a Rate Response process in accordance with embodiments herein. By way of example, the blocks illustrated in FIG. 9 may be implemented in one of, or with a combination of, hardware, circuitry, and/or microprocessors implementing firmware and/or software instructions. As a further example, the blocks illustrated in FIG. 9 may be implemented through circuitry, such as the general circuitry illustrated in FIG. 3, as may be referenced hereafter as examples. However, it is understood that the block diagram of FIG. 9 is not limited to the circuitry implementation of FIG. 3.

A blood-temperature measurement signal 901 is provided by the temperature sensor and serves as input to a Preprocessing and Baseline Removal (PBR) block 902. The PBR block 902 is configured to perform noise reduction (e.g. filtering) from the raw measurement signal 901 and to generate a Relative Temperature signal 903 that is determined or derived relative to a baseline. The Relative Temperature signal 903 is fed into three processing blocks, Onset Response 904, Short Term Response 906, and Long Term Response 908. The Onset Response 904, Short Term Response 906, and Long Term Response 908 may be implemented in parallel (as shown), in series or a combination thereof. When implemented in series, the Onset Response 904, Short Term Response 906, and Long Term Response 908 may be implemented in various orders.

The Onset Response 904 is configured to manage a rapid initial increase in heart rate based on the initial drop in the blood temperature, when the patient is in an exercise onset state (e.g., beginning to perform exercise). When an initial drop in blood temperature is detected that is indicative of an exercise onset state, the onset response 904 generates an Onset Response signal 905 indicating that the heart rate should be increased.

The Short Term Response 906 is configured to manage a target rate of increase in the heart rate relative to a rate at which the blood temperature is increasing. When an increase in blood temperature is detected, the short term response 906 analyzes the rate of change in the blood temperature over a select time period. When in an initial phase of exercisestate, the short term response 906 generates a Short Term Response signal 907 indicative of a rate of change in the target heart rate that is proportional to the rate at which the blood temperature increases.

The Long Term Response 908 is configured to manage heart rate increase during a sustained exercise state. To do so, the long-term response 908 analyzes change in the blood temperature over an extended period of time that is greater than the selected time period utilized in connection with analysis by the short term response 906. When in a sustained exercise state, the long-term response 908 generates a Long Term Response signal 909 indicating that the heart rate should be increased in a manner consistent with a sustained exercise state.

The three signals 905, 907, and 909 are provided as inputs to the Combiner 911, which combines the signals 905, 907 and 909 in a predetermined manner to form a combined response 912 that is indicative of an overall heart rate increase and/or target heart rate based on whether the patient is in an exercise onset state, an initial phase of exercise, a sustained exercise state or a non-exercise state. The Basic Rate 910 is also an input to the Combiner 911, such that when there is no need for a rate increase, the Combined Response signal 912 can be set to the Basic Rate 910.

The Combined Response signal 912 is provided as an input to the Value Limiter block 913 which functions to limit the range of values of the target heart rate for the safety of the patient. The output of the Value Limiter 914 serves as input to the Rate-of-change Limiter 915. The function of the Rate-of-change Limiter 915 is to limit the rate of change of the target heart rate thereby prevent sudden changes in heart rate. The output of the Rate-of-change Limiter 915 is the Sensor Indicated Rate 916, which is utilized by the pacemaker to set the target pacing rate.

In certain embodiments, the processing blocks are re-arranged to arrive at embodiments that work equivalently or similarly. For example, in FIG. 9, the Basic Rate 910 is shown entering the Combiner 911. Since the Basic Rate is a static value, it is possible to instead combine the Basic Rate 910 with the output of the Rate-of-change Limiter 915 and change the range of the Value Limiter 913 to achieve an equivalent result.

Each of the blocks shown in FIG. 9 may have alternative embodiments. Each embodiment may have different characteristics, which allow making tradeoffs among performance, complexity, code size, and so on. It is recognized that the various combinations of the blocks will result in alternative embodiments for the entire algorithm. The following paragraphs describe alternative embodiments of the different processing blocks, including the preferred embodiment.

Preprocessing and Baseline Removal 902:

The PBR block 902 is configured to perform preprocessing to reduce any noise in the raw temperature signal. With reference to FIG. 3 in a certain embodiment, the preprocessing may be performed by a Low Pass Filter 302. Alternative embodiments could use a different time constant, a higher order filter, a finite-impulse response (FIR) filter, a non-linear filtering (for example a median filter). The function of baseline removal is to produce the Relative Temperature signal 903, a signal that represents a displacement from a slowly varying baseline. In certain embodiments, the baseline is estimated by the Low Pass Filter 303 and baseline removal is performed by the subtraction operation 304. Alternative embodiments may use a different time constant in the low pass filter, a FIR filter, or a higher order filter. In some situations, the baseline may not change significantly during exercise, and therefore the relative signal will not change notably. Certain embodiments may limit the rate of change of the baseline filter output in addition to the low pass filter. In certain alternative embodiments, the logic 120, one or more processors or other circuits within the pacemaker, detects when exercise is occurring to hold the value of the baseline. Alternatively or additionally, the baseline can be adjusted on a daily basis in order to synchronize with the patient's daily temperature pattern.

Onset Response 904:

The Onset Response (or Dip Response) is configured to manage a rapid initial increase in a target heart rate of the pacemaker at the onset of exercise, namely when the patient is in an exercise onset state. The Onset Response 904 (or Dip Response) may be implemented by the logic 120, one or more processors or other circuitry within the pacemaker to analyze the relative temperature signal 903 to determine the temperature within the blood. A sudden drop in temperature that can occur at the start of exercise. As one example, the Onset Response 904 may be implemented as all or a portion of the Low Pass Filter 311, subtraction 312, inversion 313, and proportional limiter processing block 314. The Onset Response 904 may be processed to ensure a positive increase such as by comparator 316 and multiplier 317.

Alternative embodiments could replace the proportional limiter with another block that behaves similarly, such as a sigmoid function. The purpose of the high pass filter is to time-limit the response in the event there is a drop in temperature and the subsequent rise in temperature does not reach baseline level. An alternative embodiment could omit the filter or change the characteristics of the filter. To improve the rapidity on the onset response, another embodiment could add processing that computes the negative slope inherent in the temperature drop and use that result to augment the existing response.

Short Term Response 906:

The Short Term Response (or Slope Response) is configured to manage a rate of change in the target heart rate while the blood temperature is increasing, where the rate of change is proportional to the rate of increase in the blood temperature. Physiologically, the blood temperature rises due to the release of heat during exercise. The rate of change in the blood temperature may be indicative of the nature of the exercise and consequently an appropriate rate of change in the heart rate.

In certain embodiments, the Short Term Response signal 907 is generated by the Positive Differentiator 321 followed by multiplier 322 which scales the intermediate results by the Slope Response parameter 324. The Positive Differentiator outputs the slope that is positive and performs smoothing with a single pole low pass filter. Differentiation is performed by taking the difference of two successive sample points. Alternative embodiments could take the difference of sample points further apart or use multiple points. Moreover, different smoothing filters could be applied. In certain embodiments, a computation model of the blood core temperature without exercise is devised, and the difference between the relative temperature and that model is taken to derive an estimate of the temperature change due to exercise alone.

Long Term Response 908:

The Long Term Response (or Magnitude Response) is configured to provide a rate increase from the temperature rise due to sustained exercise. In an embodiment, the Long Term Response signal 909 is generated by a term that is proportional to the positive part of the relative temperature, using rectifier 331 and multiplier 332. Rather than using proportionality, an alternative embodiment could allow the long term response be a non-linear, such as piece-wise linear curve, function of the relative temperature. The slopes and break-points of the piece-wise linear curve would be settable parameters. Another embodiment could time-limit the long term contribution.

Combiner 911:

The Combiner 911 is configured to combine the Onset Response signal 905, Short Term Response signal 907, Long Term signal 909, and the Basic Rate 910 into a single Combined Response signal 912. In an embodiment, the Onset Response and the Short Term Response are combined by taking the larger of the two values. For example, with reference to the example circuit of FIG. 3, the onset response signal 905 and short-term response signal 907 may be combined through the divider 323 and Seed Term input to the Positive Differentiator 321. The output is combined with the Long Term Response (Magnitude Response) and the Basic Rate using the summation operator 342. An alternative embodiment could combine the Onset Response signal 905 and the Short Term response signal 907 with a different operation, for example by summation.

Value Limiter 913:

The Value Limiter 913 is configured to limit the combined response 912 to remain within a selected range, thereby limiting the Sensor Indicated Rate to values within a select range. In an embodiment, with reference to FIG. 3, the upper limit of the selected range is enforced by the Limiter block 345. A lower limit is not required because the prior computations are configured to avoid producing a value below the Basic Rate.

Rate-of-Change Limiter 915:

The Rate-of-change Limiter 915 is configured to limit the rate of change of the target pacing rate. In an embodiment, with reference to FIG. 3, limiting the rate of change in the target pacing rate may be performed by the low pass filter 346. A step change to the input to the low pass filter results in an output change with limited slope that decreases exponentially. In certain embodiments, the time constant is the same for positive and negative changes. In an alternative embodiment, different time constants may be applied for each direction. In yet another alternative embodiment, a slew limiter may be utilized instead of a low pass filter, which would limit the change (difference) of the next output value to be no more than a limiting value from the output value. A variation of this embodiment could impose different limits for decreasing and increasing changes. Moreover, the limiting values could vary depending on the current rate.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

Figure 10:
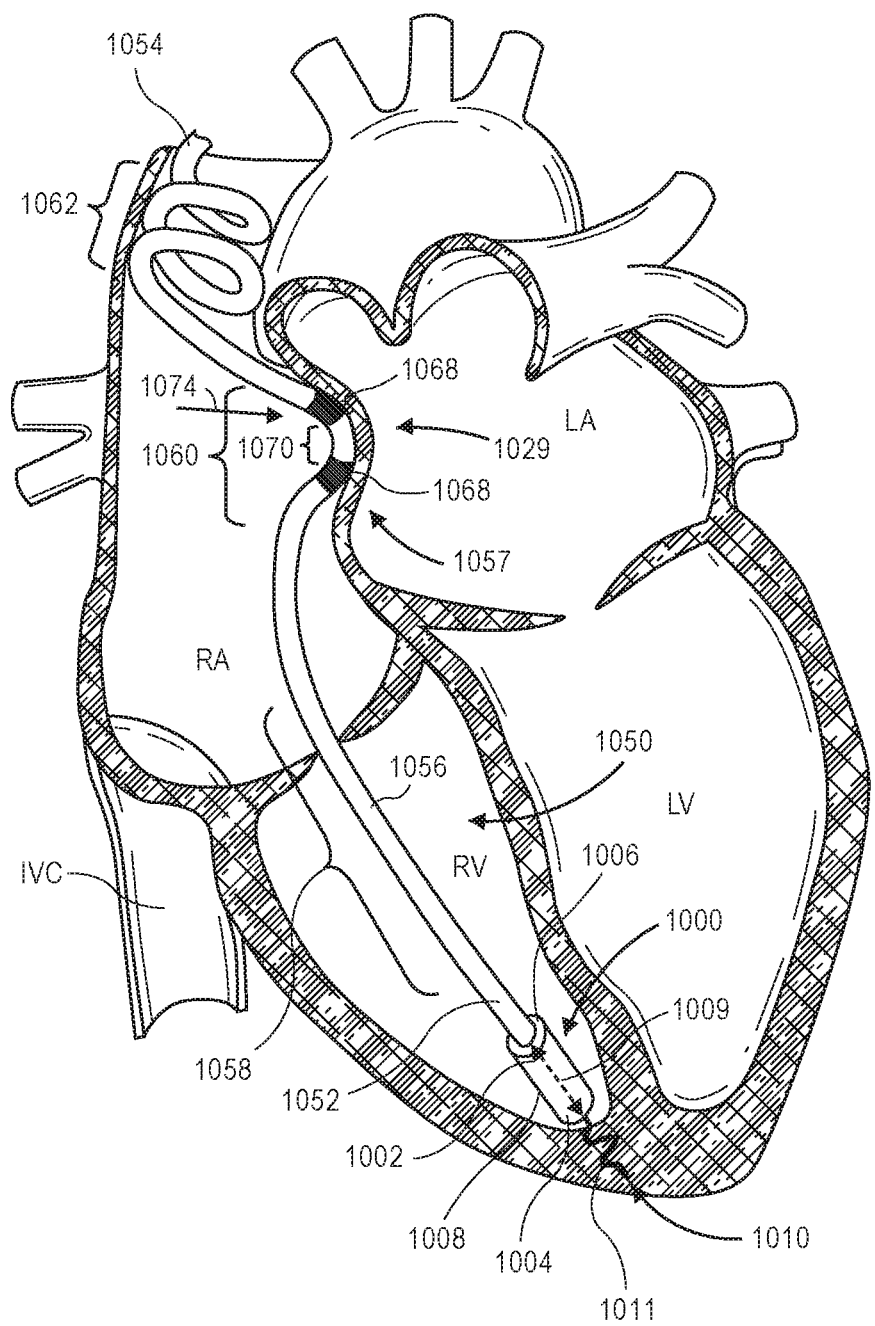
FIG. 10 is a simplified diagram of an embodiment of intra-cardiac medical device (ICMD).

FIG. 10 illustrates an intra-cardiac medical device (ICMD) 1000 formed in accordance with embodiments herein. The ICMD 1000 has been placed through the superior vena cava, through the right atrium and into the right ventricle of the heart. Optionally, the ICMD 1000 may have been introduced through the inferior vena cava. As another option, the ICMD 1000 may be introduced into the left atrium through the intra-atrial septum, into the left ventricle through the intraventricular septum, into the left ventricle through the aorta, and the like. The atrial septum divides the two atria, while the tricuspid valve is shown between the right atrium and right ventricle. FIG. 10 also illustrates the right atrial appendage 1029. The reader will appreciate that the view of FIG. 10 is simplified and somewhat schematic, but that nevertheless FIG. 10 and the other views included herein will suffice to illustrate adequately the placement and operation of certain embodiments. The term "septum" shall be used throughout to generally refer to any portion of the heart separating two chambers (e.g. RA to LA, RA to RV, RV to LV, LA to LV, RA to LV). The ICMD 1000 is formed in accordance with an embodiment and may represent a pacemaker that functions in a DDD-mode, a cardiac resynchronization device, a cardioverter, a defibrillator and the like. When in DDD-mode, the ICMD 1000 may sense in two chambers, pace in two chambers and inhibit pacing in either chamber based on intrinsic events sensed in that chamber or in the other chamber. The ICMD 1000 is configured to be implanted entirely within a single local chamber of the heart. For example, the ICMD 1000 may be implanted entirely and solely within the right atrium or entirely and solely within the right ventricle. Optionally, the ICMD 1000 may be implanted entirely and solely within the left atrium or left ventricle through more invasive implant methods.

For convenience, hereafter the chamber in which the ICMD 1000 is implanted shall be referred to as the "local" chamber. The term "adjacent" chamber shall refer to any chamber separated from the local chamber by tissue (e.g., the RV, LV and LA are adjacent chambers to the RA; the RA and LV are adjacent chambers to the LA; the RA and RV are adjacent to one another; the RV and LV are adjacent to one another, and the LV and LA are adjacent to one another).

The ICMD 1000 includes a housing 1002 that includes a base 1004 and a top end 1006. The housing 1002 extends along a longitudinal axis 1009 between the base 1004 and the top end 1006. The housing 1002 is elongated and tubular in shape and extends along the longitudinal axis 1009. The base 1004 is configured to be secured to the local chamber. In the example of FIG. 10, the base 1004 is secured to the right ventricle. Optionally, the ICMD 1000 may be located in, and the base 1004 secured to the wall of the left ventricle, left atrium or right atrium.

The base 1004 includes an active fixation member 1010 provided thereon and extending outward from the base 1004 in a direction generally along the longitudinal axis 1009. A first electrode 1011 (also referred to as an active electrode area) is provided on the active fixation member 1010. In alternative embodiments, the first electrode 1011 may be located adjacent to, but not on, the active fixation member. U.S. Pub. No. 20120158111 to Khairkhahan, which is incorporated herein by reference in its entirety, describes a fixation mechanism separate from the pacing electrode and disposed on the distal portion of the housing that may be used in accordance with certain embodiments. The electrode 1011 is provided at a first position such that, when the ICMD 1000 is implanted in the local chamber, the first electrode 1011 engages the local wall tissue at a local activation site within the conduction network of the local chamber (e.g., within the ventricular wall tissue at the apex of the right ventricle).

An intra-cardiac (IC) device extension 1050 has a proximal end 1052, a distal end 1054 and an extension body 1056 extending there between. The term "infra-cardiac" is used to indicate that the IC device extension 1050 "generally" remains within the heart and associated vessels, such as the SVC, IVC, CS, pulmonary arteries and the like. The term "device" is used to indicate that the IC device extension 1050 is an extension of the ICMD 1000. The proximal end 1052 is permanently or removably (through a header style connector) coupled to the housing 1002 and located in the local chamber. A stabilization arm, may be provided on the distal end 1052 of the extension body 1056. A right atrial appendage (RAA) fixation mechanism, generally denoted at 1057, is provided at an intermediate point along the length of the extension body 1056 and aligned with the RAA 1029. Optionally, the stabilization arm may be removed entirely and the extension body 1056 may terminate near the RAA 1029.

The temperature sensor and circuitry to analyze temperatures, as described in connection with FIGS. 1-9, may be provided in the housing 1002 and/or in the IC device extension 1050.

In the example of FIG. 10, the extension body 1056 including a chamber transition sub-segment 1058, an active interim-segment 1060 and a stabilizer end-segment 1062. The stabilization end-segment 1062 is one exemplary structural implementation of the stabilization arm. The RAA fixation mechanism 1057 is one exemplary structural implementation of an active interim-segment 1060. The chamber transition sub-segment 1058 is sufficient in length to extend from the local chamber (e.g., the right ventricle) through the tricuspid valve into an adjacent chamber (e.g., the right atrium). The chamber transition sub-segment 1058 extends upward out of the right ventricle in a direction that generally follows the longitudinal axis 1009.

The extension body 1056 is formed of a biocompatible insulated material such as EFTE, silicon, OPTIM and the like. In general, the extension body 1056 is formed of materials that are flexible yet exhibit a desired degree of shape memory such that once implanted, the active interim-segment 1060 and stabilizer end-segment 1062 are biased to return to a pre-formed shape. One or more insulated conductive wires are held within the extension body 1056 and span from the ICMD 1000 to any sensors or electrodes provided on the extension body 1056.

The stabilizer end-segment 1062 is located at the distal end 1054 and in a pre-formed shape that is biased to extend slightly outward in a lateral direction (generally denoted at 1064) relative to a length of the chamber in which the stabilizer end-segment 1062 is located. The stabilizer end-segment 1062 engages a first region of the heart. For example, the stabilizer end-segment 1062 may extend upward into and engage the SVC. Optionally, the stabilizer end-segment 1062 may extend downward into and engage the IVC. Optionally, the stabilizer end segment 1062 may extend into the coronary sinus, pulmonary artery and the like.

The stabilizer end-segment 1062 is pre-formed into a predetermined shape based upon which portion of the chamber is to be engaged. The flexible stabilizer end-segment 1062 may be wrapped into at least one turn having a pre-formed diameter. For example, when intended to securely engage the SVC, the stabilizer end-segment 1062 may be formed into a spiral shape with one or more windings or turns that are pre-disposed or biased to radially expand to a diameter sufficient to firmly fit against the interior walls of the SVC.

Optionally, the stabilizer end-segment 1062 may utilize alternative shapes for SVC stabilization, such as an S-shape, a T-shape, a Y-shape, a U-shape and the like. Optionally, the stabilizer end-segment 1062 may be split into multiple (e.g., 2-4) stabilizer end-segments that project outward in different directions and contact different areas of the wall tissue. A conductor wire extends within the extension body 1056 from the ICMD to the second electrode, and the conductor terminates at the second electrode such that the stabilizer end segment 1062 is void of electrodes and conductor wires. When the stabilizer end-segment 1062 lacks any sensors or electrodes, the stabilizer end-segment 1062 will also lack any internal conductive wires.

Optionally, the stabilizer end-segment 1062 may include one or more conductors, spanning from the distal end 1054 to the ICMD 1000, to be coupled to a programmer during implantation to provide communications, power, remote access to electrodes and the like.

The active interim-segment 1060 includes one or more electrodes 1068 that are provided thereon and in a trough area 1074 of the C-shape or U-shape. The electrodes 1068 are spaced apart from one another, within the trough area 1074, by an inter-electrode spacing 1070. For example, the second electrodes 1068 may be biased to engage wall tissue in the right atrial appendage 1029. The second electrodes 1068 engage distal wall tissue at a distal activation site (relative to the chamber which the ICMD 1000 is implanted) within the conduction tissue of the adjacent chamber. Optionally, tines or other active fixation members may be included around the hump or trough portion of the active interim-segment 1060 in order to improve fixation as the RAA fixation mechanism.

As discussed below, a controller is provided within the housing 1002 to cause stimulus pulses to be delivered, in a dual chamber synchronous manner, through the first and second electrodes 1011, 1068 to the local and distal activation sites, respectively. The stimulus pulses delivered at the distal activation site are timed to cause contraction of the adjacent chamber in a predetermined relation to contraction of the local chamber. For example, the ICMD 1000 may be configured to control delivery of the stimulus pulses from the first and second electrodes 1011, 1068 in accordance with a DDD pacing mode to a right atrium and right ventricle, while the ICMD is entirely located in one of the right atrium and right ventricle. For example, the controller may be configured to control delivery of the stimulus pulses from the first and second electrodes 1011, 1068 in accordance with a DDD pacing mode to a left atrium and left ventricle, while the ICMD is entirely located in one of the left atrium and left ventricle.

Figure 11:
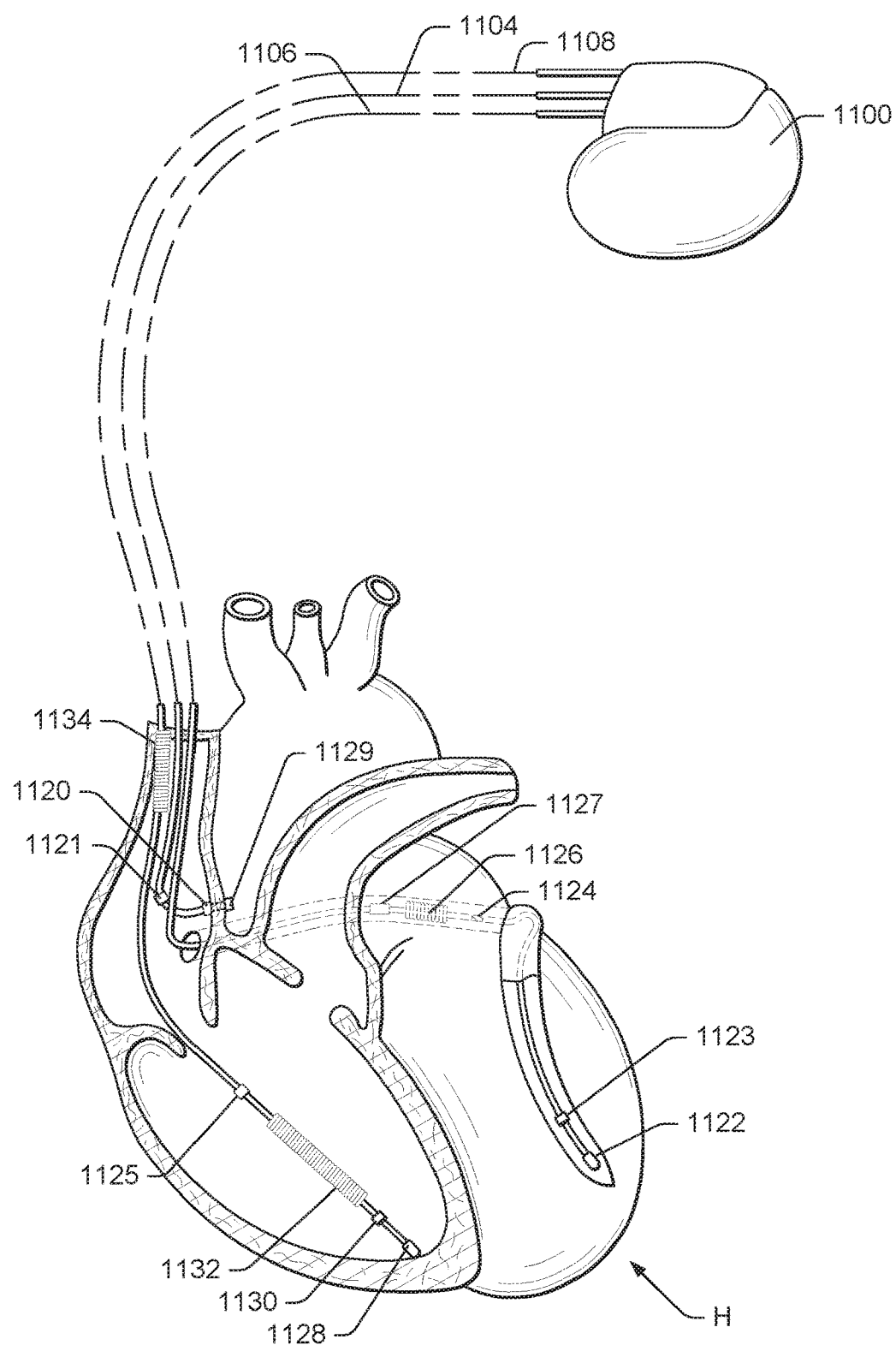
FIG. 11 is a simplified diagram of an embodiment of an implantable stimulation device in electrical communication with one or more leads implanted in a patient's heart for sensing conditions in the patient, delivering therapy to the patient, or providing some combination thereof.

FIG. 11 illustrates a cardiac pacemaker and/or implantable cardioverter-defibrillator (ICD) that utilizes one or more electrically-conductive leads that traverses blood vessels and heart chambers in order to connect a canister with electronics and a power source (the can) to electrodes affixed to the heart for the purpose of electrically exciting cardiac tissue and measuring myocardial electrical activity formed in accordance with embodiments herein. In certain alternative embodiments, a subcutaneous ICD that does not use endocardial, transvenous, or epicardial lead wires and can deliver defibrillation using subcutaneous electrodes formed in accordance with embodiments herein. For a more detailed description of a subcutaneous ICD, the reader is directed to U.S. Pat. No. 7,925,343, "Subcutaneous implantable cardiac device system with low defibrillation thresholds and improved sensing" (Min), which is incorporated herein by reference.

In FIG. 11 temperature sensing may be performed in conjunction with an implantable cardiac device (e.g., a stimulation device such as an implantable cardioverter defibrillator, a pacemaker, etc.). Here, one or more of the operations described above may be implemented in or in conjunction with such an implantable cardiac device. It should be appreciated that this example is provided for explanatory purposes and that temperature sensing may be implemented using other types of devices.

FIG. 11 illustrates an implantable cardiac device 1100 in electrical communication with a patient's heart H by way of three leads 1104, 1106, and 1108, suitable for delivering multi-chamber stimulation and shock therapy. To sense atrial cardiac signals and to provide right atrial chamber stimulation therapy, the device 1100 is coupled to an implantable right atrial lead 1104 having, for example, an atrial tip electrode 1120, which typically is implanted in the patient's right atrial appendage or septum. FIG. 11 also shows the right atrial lead 1104 as having an optional atrial ring electrode 1121.

To sense left atrial and ventricular cardiac signals and to provide left chamber pacing therapy, device 1100 is coupled to a coronary sinus lead 1106 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 1106 is designed to receive atrial and ventricular cardiac signals and to deliver left ventricular pacing therapy using, for example, a left ventricular tip electrode 1122 and, optionally, a left ventricular ring electrode 1123; provide left atrial pacing therapy using, for example, a left atrial ring electrode 1124; and provide shocking therapy using, for example, a left atrial coil electrode 1126 (or other electrode capable of delivering a shock). For a more detailed description of a coronary sinus lead, the reader is directed to U.S. Pat. No. 5,466,254, "Coronary Sinus Lead with Atrial Sensing Capability" (Helland), which is incorporated herein by reference.

The device 1100 is also shown in electrical communication with the patient's heart H by way of an implantable right ventricular lead 1108 having, in this implementation, a right ventricular tip electrode 1128, a right ventricular ring electrode 1130, a right ventricular (RV) coil electrode 1132 (or other electrode capable of delivering a shock), and a superior vena cava (SVC) coil electrode 1134 (or other electrode capable of delivering a shock). Typically, the right ventricular lead 1108 is transvenously inserted into the heart H to place the right ventricular tip electrode 1128 in the right ventricular apex so that the RV coil electrode 1132 will be positioned in the right ventricle and the SVC coil electrode 1134 will be positioned in the superior vena cava. Accordingly, the right ventricular lead 1108 is capable of sensing or receiving cardiac signals, and delivering stimulation in the form of pacing and shock therapy to the right ventricle.

Any of the leads 1104, 1106, and 1108 may include one or more temperature sensors as taught herein. Temperature signals generated by a temperature sensor may be transmitted to the device 1100 via one or more conductors that run through a corresponding cardiac lead. The device 1100 may then utilize the corresponding temperature readings to commence or alter therapy for the patient, or to forward the temperature information or sensor indicated rate response or other programming information to an external device, such as a leadless pacemaker or a programmer external to the patient.

In certain embodiments, conductors associated with other components of the lead 1108 (e.g., electrodes 1128, 1130, and 1132) may be routed through the passageway(s) in the bottom portion of the sensor assembly.

It should be appreciated that temperature may be measured in various chambers of the heart or related vessels and that other mechanisms may be employed to measure temperature in a given chamber or vessel.

The device 1100 may connect to leads other than those specifically shown. In addition, the leads connected to the device 1100 may include components other than those specifically shown. For example, a lead may include other types of electrodes, sensors or devices that serve to otherwise interact with a patient or the surroundings.

In some embodiments, code including instructions (e.g., software, firmware, middleware, etc.) may be executed on one or more processing devices to implement one or more of the described functions or components. The code and associated components (e.g., data structures and other components by the code or to execute the code) may be stored in an appropriate data memory that is readable by a processing device (e.g., commonly referred to as a computer-readable medium).

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, implemented as discrete wires, or in other ways.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

Figure 12:
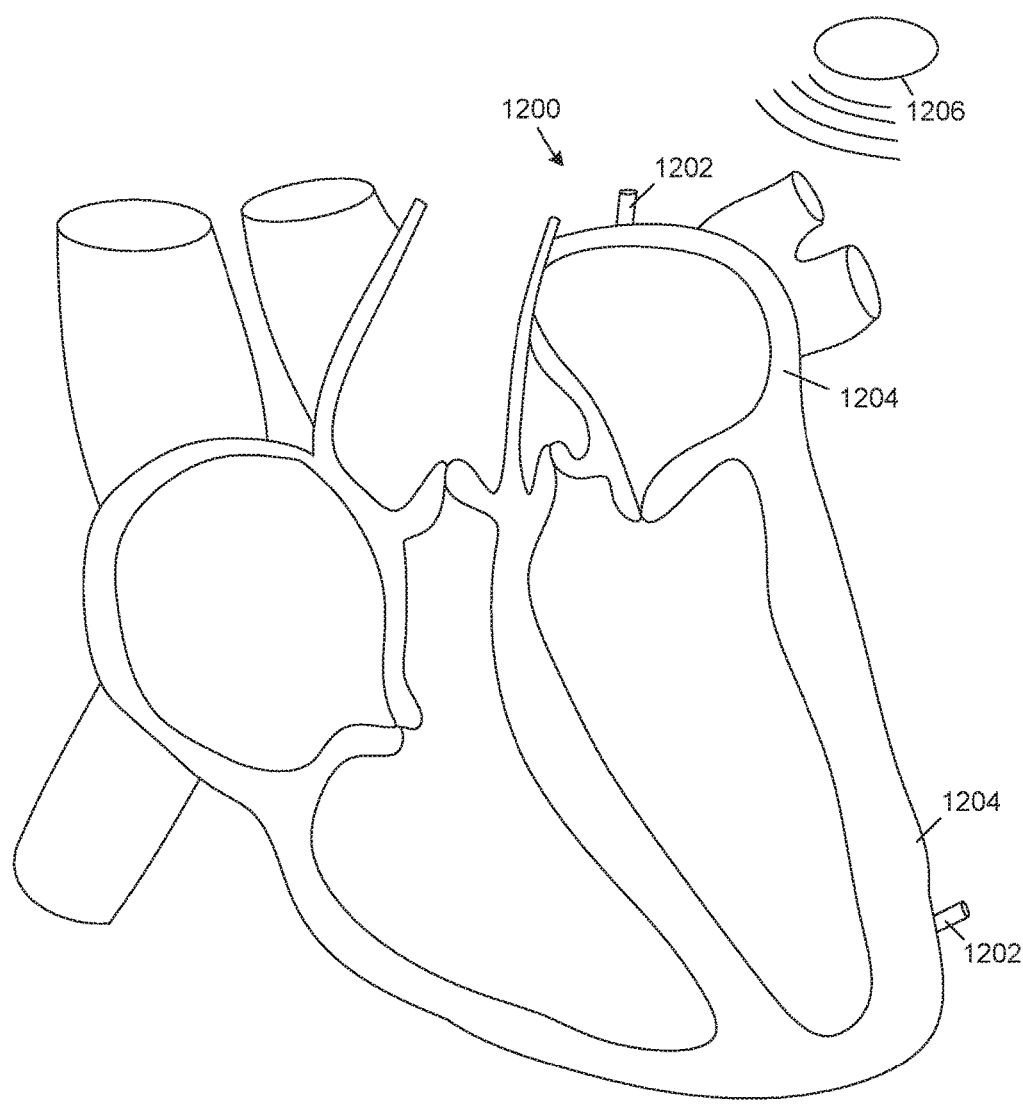
FIG. 12 is a simplified diagram illustrating an example of a cardiac rhythm management system formed in accordance with embodiments herein.

Referring to FIG. 12, a pictorial diagram shows an embodiment of a cardiac pacing system 1200 including one or more leadless cardiac pacemakers 1202 with conducted communication for performing cardiac pacing in conjunction with an implantable cardioverter-defibrillator (ICD) 1206. The system 1200 can implement for example single-chamber pacing, dual-chamber pacing, or three-chamber pacing for cardiac resynchronization therapy, without requiring pacing lead connections to the defibrillator 1206. The illustrative cardiac pacing system 1200 comprises at least one leadless cardiac pacemaker 1202 configured for implantation in electrical contact with a cardiac chamber 1204 and configured to perform cardiac pacing functions in combination with a co-implanted implantable cardioverter-defibrillator (ICD) 1206. One or more of the leadless cardiac pacemakers 1202 can comprise at least two leadless electrodes 1208 configured for delivering cardiac pacing pulses, sensing evoked and/or natural cardiac electrical signals, and uni-directionally or bi-directionally communicating with the co-implanted ICD 1206.

According to certain embodiments, a temperature sensor may be provided in the housing or integrally attached to the housing of one or more of the leadless pacemakers 1202 and circuitry to analyze temperature signals generated by the temperature sensor may be provided in the housing of the ICD 1206, which may be a subcutaneous ICD. According to certain embodiments, circuitry to analyze temperatures may be provided in the housing of one of the leadless pacemakers 1202 and the temperature sensor may be located in the other leadless pacemakers 1202. Other variations of the placement of the temperature sensors and circuitry to analyze the temperature, given the disclosure herein, will be understood by one of skill in the art.

Also, it should be understood that any reference to elements herein using a designation such as "first," "second," and so forth does not generally limit the quantity or order of those elements. Rather, these designations may be used herein as a convenient method of distinguishing between two or more different elements or instances of an element. Thus, a reference to first and second elements does not mean that only two elements may be employed there or that the first element must precede the second element in some manner. Also, unless stated otherwise a set of elements may comprise one or more elements. In addition, terminology of the form "at least one of A, B, or C" or "one or more of A, B, or C" or "at least one of the group consisting of A, B, and C" used in the description or the claims means "A or B or C or any combination of these elements." For example, this terminology may include A, or B, or C, or A and B, or A and C, or A and B and C, or 2A, or 2B, or 2C, and so on.

As used herein, the term "determining" encompasses a wide variety of actions. For example, "determining" may include calculating, computing, processing, deriving, investigating, looking up (e.g., looking up in a table, a database or another data structure), ascertaining, and the like. Also, "determining" may include receiving (e.g., receiving information), accessing (e.g., accessing data in a memory), and the like. Also, "determining" may include resolving, selecting, choosing, establishing, and the like.

While certain embodiments have been described above in detail and shown in the accompanying drawings, it is to be understood that such embodiments are merely illustrative of and not restrictive of the teachings herein. In particular, it should be recognized that the teachings herein apply to a wide variety of apparatuses and methods. It will thus be recognized that various modifications may be made to the illustrated embodiments or other embodiments, without departing from the broad scope thereof. In view of the above, it will be understood that the teachings herein are intended to cover any changes, adaptations or modifications that are within the scope of the disclosure.

The blocks, modules, and controllers described herein may be implemented in various manners, such as through one or more of dedicated hardware, circuitry (integrated or discrete), firmware and/or microprocessor based architectures. One or more of the blocks, modules, and controllers described herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the (module/controller) represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The blocks, modules, and controllers may execute a set of instructions that are stored in one or more storage elements, in order to process data. The storage elements may also store data or other information as desired or needed. The storage element may be in the form of an information source or a physical memory element within the blocks, modules, and controllers. The set of instructions may include various commands that instruct the (module/controller) to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Unless defined otherwise, all technical terms used herein have the same meanings as commonly understood by one of ordinary skill in the art of cardiac technologies. Specific methods, devices, and materials may be described in this application, but any methods and materials similar or equivalent to those described herein can be used in the practice of the present invention. While embodiments of the invention have been described in some detail and by way of exemplary illustrations, such illustration is for purposes of clarity of understanding only, and is not intended to be limiting. Various terms have been used in the description to convey an understanding of the invention; it will be understood that the meaning of these various terms extends to common linguistic or grammatical variations or forms thereof. It will also be understood that when terminology referring to devices, equipment, or drugs that have been referred to by trade names, brand names, or common names, that these terms or names are provided as contemporary examples, and the invention is not limited by such literal scope. Terminology that is introduced at a later date that may be reasonably understood as a derivative of a contemporary term or designating of a hierarchal subset embraced by a contemporary term will be understood as having been described by the now contemporary terminology. Further, while some theoretical considerations have been advanced in furtherance of providing an understanding of the invention, the claims to the invention are not bound by such theory. Moreover, any one or more features of any embodiment of the invention can be combined with any one or more other features of any other embodiment of the invention, without departing from the scope of the invention. Still further, it should be understood that the invention is not limited to the embodiments that have been set forth for purposes of exemplification, but is to be defined only by a fair reading of claims that are appended to the patent application, including the full range of equivalency to which each element thereof is entitled.

It should be appreciated from the above that the various structures and functions described herein may be incorporated into a variety of apparatuses (e.g., a lead, a monitoring device, a stimulation device, etc.) and implemented in a variety of ways. Different embodiments of the biostimulator may include a variety of hardware and software processing components. In some embodiments, hardware components such as processors, controllers, state machines, logic, or some combination of these components, may be used to implement the described components or circuits.

In some embodiments, code including instructions (e.g., software, firmware, middleware, etc.) may be executed on one or more processing devices to implement one or more of the described functions or components. The code and associated components (e.g., data structures and other components by the code or to execute the code) may be stored in an appropriate data memory that is readable by a processing device (e.g., commonly referred to as a computer-readable medium).

Moreover, some of the operations described herein may be performed by a device that is located externally with respect to the body of the patient. For example, an implanted device may simply send raw data or processed data to an external device that then performs the necessary processing.

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, implemented as discrete wires, or in other ways.

The recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

What is claimed is:

1. A method for providing a temperature-based rate response to a medical device, comprising the steps of:
   sensing a blood-temperature signal;
   processing said blood-temperature signal to provide a relative-temperature signal (RTS);
   processing said RTS to provide a dip response, a slope response, and magnitude response;
   combining said dip, slope, and magnitude responses to provide a sensor-indicated rate response, where the dip, slope, and magnitude responses are responsive to said RTS; and
   automatically adjusting a pacing rate of the medical device based on the sensor-indicated rate response, wherein processing said blood-temperature signal to provide a RTS comprises:
   sampling the blood temperature signal;
   low pass filtering the blood temperature signal to determine a short-term average of the blood-temperature signal (STA);
   low pass filtering the blood temperature signal to determine a long-term average of the blood-temperature signal (LTA);
   providing the STA to a non-inverting input of an adder;
   providing the LTA to an inverting input of the adder; and
   determining the RTS by adding the non-inverted STA and inverted LTA using the adder.

2. The method of claim 1, wherein the sensor indicated rate response is determined to be a limited, proportional, and temporary rate increase when there is a dip in the blood temperature signal.

3. The method of claim 1, wherein the sensor indicated rate response is determined to be a proportional rate increase when there is a positive slope in the blood temperature signal.

4. The method of claim 1, wherein the sensor indicated rate response is determined to be a proportional rate increase when the relative-temperature signal is a positive magnitude.

5. The method of claim 1, wherein the sensor indicated rate response is determined to be the slope response seeded with the dip response when there is a transition between a dip in the blood temperature signal and a positive slope in the blood temperature signal.

6. The method of claim 1, wherein processing said RTS to provide the dip response comprises:
   applying the RTS to non-inverting input of an adder;
   low pass filtering the RTS with a dip time constant;
   applying low pass filtered RTS to inverting input of the adder;
   calculating high-pass filtered RTS using the adder;
   applying high-pass filtered RTS to an inverter;
   applying output of the inverter to a proportional limiter;
   providing a dip response adjustment to a proportional limiter;
   applying the RTS to a comparator;
   determining whether the RTS is less than zero;
   setting the output of the comparator to 1 if the RTS is less than zero;
   setting the output of the comparator to 0 if the RTS is not less than zero;
   applying output of the proportional limiter and the comparator to a dip response multiplier; and
   calculating the dip response using the multiplier.

7. The method of claim 1, wherein processing said RTS to provide the slope response comprises:
   dividing the dip response output by a slope response adjustment yielding a seed term;
   applying the seed term to a positive differentiator;
   applying the RTS to the positive differentiator;
   calculating an output of the positive differentiator; and
   multiplying the output of the positive differentiator with a slope response adjustment.

8. The method of claim 7, wherein calculating an output of the positive differentiator comprises:
   determining whether the input (in) of the positive differentiator is less than state $+\alpha^*$ seed;
   if in is less than state $+\alpha^*$ seed, setting state to in $-\alpha^*$ seed and setting the output of the positive differentiator to seed; and
   if in is not less than state $+\alpha^*$ seed, setting a temporary variable new_state to in/$\alpha$+state* $(1-1/\alpha)$, setting the output of the positive differentiator to new_state−state, and setting state to new_state.

9. The method of claim 1, wherein processing said RTS to provide the magnitude response comprises:
   determining whether the RTS is less than zero;
   if the RTS is less than zero, setting the magnitude response to zero; and
   if the RTS is not less than zero, multiplying the RTS by a magnitude response adjustment to yield the magnitude response.

10. The method of claim 1, wherein combining said dip, slope, and magnitude responses to provide a sensor-indicated rate response comprises:
    adding a basic rate adjustment to the slope response output and the magnitude response output to yield a sum;
    determining whether the sum is greater than a maximum sensor adjustment rate;
    if the sum is not greater than the maximum sensor adjustment rate, applying the sum to a low pass filter to yield the sensor indicated rate;
    if the sum is greater than the maximum sensor rate, applying the maximum sensor adjustment rate to a low pass filter to yield the sensor indicated rate.

11. A method for providing a temperature-based rate response to a medical device, comprising the steps of:
    sensing a blood-temperature signal;
    processing said blood-temperature signal to provide a relative-temperature signal (RTS);
    processing said RTS to provide a dip response, a slope response, and magnitude response;
    combining said dip, slope, and magnitude responses to provide a sensor-indicated rate response, where the dip, slope, and magnitude responses are responsive to said RTS; and
    automatically adjusting a pacing rate of the medical device based on the sensor-indicated rate response, wherein the sensor indicated rate response is determined to be the slope response seeded with the dip response when there is a transition between a dip in the blood temperature signal and a positive slope in the blood temperature signal.

12. The method of claim 11, wherein processing said blood-temperature signal to provide a RTS comprises:
sampling the blood temperature signal;
low pass filtering the blood temperature signal to determine a short-term average of the blood-temperature signal (STA);
low pass filtering the blood temperature signal to determine a long-term average of the blood-temperature signal (LTA);
providing the STA to a non-inverting input of an adder;
providing the LTA to an inverting input of the adder; and
determining the RTS by adding the non-inverted STA and inverted LTA using the adder.

13. The method of claim 11, wherein processing said RTS to provide a dip response comprises:
applying the RTS to non-inverting input of an adder;
low pass filtering RTS with a dip time constant;
applying low pass filtered RTS to inverting input of the adder;
calculating high-pass filtered RTS using the adder;
applying high-pass filtered RTS to an inverter;
applying output of the inverter to a proportional limiter;
providing a dip response adjustment to a proportional limiter;
applying the RTS to a comparator;
determining whether the RTS is less than zero;
setting the output of the comparator to 1 if the RTS is less than zero;
setting the output of the comparator to 0 if the RTS is not less than zero;
applying output of the proportional limiter and the comparator to a dip response multiplier; and
calculating the dip response using the multiplier.

14. The method of claim 11, wherein processing said RTS to provide the slope response comprises:
dividing the dip response output by a slope response adjustment yielding a seed term;
applying the seed term to a positive differentiator;
applying the RTS to the positive differentiator;
calculating an output of the positive differentiator; and
multiplying the output of the positive differentiator with a slope response adjustment.

15. The method of claim 14, wherein calculating an output of the positive differentiator comprises:
determining whether the input (in) of the positive differentiator is less than state +α* seed;
if in is less than state +α* seed, setting state to in −α* seed and setting the output of the positive differentiator to seed; and
if in is not less than state +α* seed, setting a temporary variable new_state to in/α+state* (1-1/α), setting the output of the positive differentiator to new_state−state, and setting state to new_state.

16. A method for providing a temperature-based rate response to a medical device, comprising the steps of:
sensing a blood-temperature signal;
processing said blood-temperature signal to provide a relative-temperature signal (RTS);
processing said RTS to provide a dip response, a slope response, and magnitude response;
combining said dip, slope, and magnitude responses to provide a sensor-indicated rate response, where the dip, slope, and magnitude responses are responsive to said relative-temperature signal; and
automatically adjusting a pacing rate of the medical device based on the sensor-indicated rate response, wherein processing said RTS to provide a dip response comprises:
applying the RTS to non-inverting input of an adder;
low pass filtering the RTS with a dip time constant;
applying low pass filtered RTS to inverting input of the adder;
calculating high-pass filtered RTS using the adder;
applying high-pass filtered RTS to an inverter;
applying output of the inverter to a proportional limiter;
providing a dip response adjustment to a proportional limiter;
applying the RTS to a comparator;
determining whether the RTS is less than zero;
setting the output of the comparator to 1 if the RTS is less than zero;
setting the output of the comparator to 0 if the RTS is not less than zero;
applying output of the proportional limiter and the comparator to a dip response multiplier; and
calculating the dip response using the multiplier.

17. A method for providing a temperature-based rate response to a medical device, comprising the steps of:
sensing a blood-temperature signal;
processing said blood-temperature signal to provide a relative-temperature signal (RTS);
processing said RTS to provide a dip response, a slope response, and magnitude response;
combining said dip, slope, and magnitude responses to provide a sensor-indicated rate response, where the dip, slope, and magnitude responses are responsive to said relative-temperature signal; and
automatically adjusting a pacing rate of the medical device based on the sensor-indicated rate response, wherein processing said RTS to provide the slope response comprises:
dividing the dip response output by a slope response adjustment yielding a seed term;
applying the seed term to a positive differentiator;
applying the RTS to the positive differentiator;
calculating an output of the positive differentiator; and
multiplying the output of the positive differentiator with a slope response adjustment.

18. The method of claim 17, wherein calculating an output of the positive differentiator comprises:
determining whether the input (in) of the positive differentiator is less than state +α* seed;
if in is less than state +α* seed, setting state to in −α* seed and setting the output of the positive differentiator to seed; and
if in is not less than state +α* seed, setting a temporary variable new_state to in/α+state* (1-1/α), setting the output of the positive differentiator to new_state−state, and setting state to new_state.

19. A method for providing a temperature-based rate response to a medical device, comprising the steps of:
sensing a blood-temperature signal;
processing said blood-temperature signal to provide a relative-temperature signal (RTS);
processing said RTS to provide a dip response, a slope response, and a magnitude response;
combining said dip, slope, and magnitude responses to provide a sensor-indicated rate response, where the dip, slope, and magnitude responses are responsive to said RTS; and automatically adjusting a pacing rate of the medical device based on the sensor-indicated rate response, wherein processing said RTS to provide the magnitude response comprises:

determining whether the RTS is less than zero;

if the RTS is less than zero, setting the magnitude response to zero; and if the RTS is not less than zero, multiplying the RTS by a magnitude response adjustment to yield the magnitude response.

20. The method of claim 19, wherein the sensor indicated rate response is determined to be the slope response seeded with the dip response when there is a transition between a dip in the blood temperature signal and a positive slope in the blood temperature signal.

* * * * *